(12) United States Patent
Miyamoto et al.

(10) Patent No.: US 7,947,035 B2
(45) Date of Patent: May 24, 2011

(54) INSTRUMENT FOR ENDOSCOPE HAVING PIVOTABLE OFFSET PORTIONS

(75) Inventors: Manabu Miyamoto, Tokyo (JP); Takumi Dejima, Tokyo (JP); Ryo Minosawa, Tsukui-gun (JP); Kiyotaka Matsuno, Sagamihara (JP); Tatsutoshi Hashimoto, Tokyo (JP)

(73) Assignee: Olympus Medical Systems Corp. (JP)

( * ) Notice: Subject to any disclaimer, the term of this patent is extended or adjusted under 35 U.S.C. 154(b) by 820 days.

(21) Appl. No.: 11/399,214

(22) Filed: Apr. 6, 2006

(65) Prior Publication Data
US 2007/0260114 A1    Nov. 8, 2007

Related U.S. Application Data

(63) Continuation-in-part of application No. 11/237,479, filed on Sep. 27, 2005, now abandoned.

(51) Int. Cl.
*A61B 17/00* (2006.01)
(52) U.S. Cl. ............................................. 606/1; 600/104
(58) Field of Classification Search ............. 606/1, 205, 606/207, 104, 114, 139, 141–143, 146, 150, 606/106, 250, 251, 253, 259; 600/114, 129, 600/142, 146, 104
See application file for complete search history.

(56) References Cited

U.S. PATENT DOCUMENTS

| 4,950,273 | A | 8/1990 | Briggs |
| 5,395,367 | A | 3/1995 | Wilk |
| 5,558,665 | A | 9/1996 | Kieturakis |
| 5,607,435 | A | 3/1997 | Sachdeva et al. |
| 5,626,607 | A | 5/1997 | Malecki et al. |
| 5,766,184 | A | 6/1998 | Matsuno et al. |
| 5,787,897 | A | 8/1998 | Kieturakis |
| 5,855,590 | A * | 1/1999 | Malecki et al. ............... 606/205 |
| 6,152,871 | A | 11/2000 | Foley et al. |
| 6,245,085 | B1 | 6/2001 | Benecke et al. |

(Continued)

FOREIGN PATENT DOCUMENTS
DE    43 24 254    1/1995
(Continued)

OTHER PUBLICATIONS

Letter from Associates reporting the European Search Report dated Aug. 9, 2007.
(Continued)

*Primary Examiner* — John P Leubecker
*Assistant Examiner* — Victoria W Chen
(74) *Attorney, Agent, or Firm* — Ostrolenk Faber LLP

(57) ABSTRACT

An instrument for an endoscope includes a first insertion portion having an base end to which an operation section is connected; a first offset portion extending outward from an axis of the first insertion portion; a second insertion portion having a base end joined to the first offset portion and an element extending parallel to the axis of the first insertion portion; a second offset portion which is joined to a head of the second insertion portion and reaches an extension of the axis of the first insertion portion; a third insertion portion which is joined to the second offset portion and has a portion arranged on an axis which is substantially the same as at least a part of the axis of the first insertion portion; and an inner hole formed through the first insertion portion, the first offset portion, the second insertion portion, the second offset portion, and the third insertion portion.

12 Claims, 25 Drawing Sheets

U.S. PATENT DOCUMENTS

| | | |
|---|---|---|
| 6,447,444 B1 | 9/2002 | Avni et al. |
| 6,575,899 B1 | 6/2003 | Foley et al. |
| 6,585,639 B1 | 7/2003 | Kotmel et al. |
| 6,603,994 B2 | 8/2003 | Wallace et al. |
| 6,679,833 B2 | 1/2004 | Smith et al. |
| 6,705,989 B2 * | 3/2004 | Cuschieri et al. ............. 600/208 |
| 6,783,491 B2 | 8/2004 | Saadat et al. |
| 7,553,275 B2 * | 6/2009 | Padget et al. ................. 600/142 |
| 2003/0220654 A1 | 11/2003 | Pineda et al. |
| 2004/0019252 A1 | 1/2004 | Hirata |
| 2004/0054322 A1 | 3/2004 | Vargas |
| 2004/0059253 A1 | 3/2004 | Martone et al. |
| 2005/0096694 A1 | 5/2005 | Lee |
| 2005/0107669 A1 * | 5/2005 | Couvillon .................... 600/146 |
| 2005/0149047 A1 | 7/2005 | Parry et al. |
| 2005/0250988 A1 | 11/2005 | Ewers et al. |
| 2005/0273085 A1 | 12/2005 | Hinman et al. |
| 2006/0235368 A1 | 10/2006 | Oz |

FOREIGN PATENT DOCUMENTS

| | | |
|---|---|---|
| EP | 1 342 451 | 9/2003 |
| JP | 08-238250 | 9/1996 |
| JP | 2005-523764 | 8/2005 |
| WO | WO 96/39944 | 12/1996 |
| WO | WO 98/48687 | 11/1998 |
| WO | WO 99/15089 | 4/1999 |
| WO | WO 03/092513 | 11/2003 |
| WO | WO03/092513 | 11/2003 |
| WO | WO 2006/100658 | 9/2006 |

OTHER PUBLICATIONS

European Search Report dated Aug. 2, 2007 connection with corresponding European Patent Application No.: EP 07 00 5849.

Office Action issued by Japanese Patent Office on Apr. 23, 2010 in connection with corresponding Japanese application No. 2007-069228 and English translation thereof.

Search Report issued by European Patent Office in connection with corresponding application No. EP 10 01 0940 on Nov. 25, 2010.

Notice of Allowance Action issued by Japanese Patent Office on Jul. 6, 2010 in connection with corresponding Japanese application 2007-069228 and English translation thereof.

* cited by examiner

INSTRUMENT FOR ENDOSCOPE HAVING PIVOTABLE OFFSET PORTIONS

CROSS REFERENCE TO RELATED APPLICATION

This application is a continuation in part of U.S. patent application Ser. No. 11/237,479 filed Sep. 27, 2005 entitled INSTRUMENT FOR ENDOSCOPE.

BACKGROUND OF THE INVENTION

1. Field of the Invention

The present invention relates to an instrument used together with an endoscope in a surgical operation using the endoscope.

2. Description of the Related Art

In a surgical operation using an endoscope, treatment tools such as forceps are used. An example of the treatment tool is disclosed in U.S. Pat. No. 6,245,085. In an operation using such a treatment tool, a hole (called a "port") having a diameter of 5 to 10 mm is provided in a body wall, and the treatment tool is inserted through the hole. In this case, the area where treatment is possible is narrower in comparison with an open operation in which a portion of a body wall is cut and opened. Therefore, when an area to be treated is large or the position of the hole is inappropriate with respect to the part to be treated, the operation of the treatment tool may be difficult, or the treatment may be complicated. In such a case, if another hole is provided at another position, the damaged area in the patient's body is increased in size.

PCT International Publication, No. WO98/48687 discloses a treatment tool for solving the above problems. In the disclosed treatment tool, a treatment section and an operation section are not coaxially arranged. When using such a treatment tool, it is difficult for the operator to intuitively know the position to be treated. Additionally, a possible amount of offset between the treatment section and an inserted portion is restricted depending on the outer diameter of the hole provided in a body wall. In order to secure a sufficiently wide area which can be treated, the diameter of the hole must be large. Therefore, it is difficult to perform wide area treatment with low damage.

SUMMARY OF THE INVENTION

The present invention provides an instrument for an endoscope, which includes:

a first insertion portion having an base end portion to which an operation section is connected;

a first offset portion extending outward from an axis of the first insertion portion;

a second insertion portion having a base end portion joined to the first offset portion and an element extending parallel to the axis of the first insertion portion;

a second offset portion which is joined to a head portion of the second insertion portion and reaches an extension of the axis of the first insertion portion;

a third insertion portion which is joined to the second offset portion and has a portion arranged on an axis which is substantially the same as at least a part of the axis of the first insertion portion; and an inner hole formed through the first insertion portion, the first offset portion, the second insertion portion, the second offset portion, and the third insertion portion.

The present invention also provides a medical instrument including:

a first insertion portion having a base end at which an operation section for operating the device is provided;

a second insertion portion positioned at a head side of the first insertion portion;

a third insertion portion which is positioned at a head side of the second insertion portion and has a head at which a device for performing medical treatment is provided;

a first movable joint portion for coupling the first insertion portion and the second insertion portion with each other in a manner such that a first position in which axes of the first insertion portion and the second insertion portion approach each other and a second position in which the axes of the first insertion portion and the second insertion portion are away from each other are freely switchable;

a second movable joint portion for coupling the second insertion portion and the third insertion portion with each other in a manner such that a first position in which axes of the second insertion portion and the third insertion portion approach each other and a second position in which the axes of the second insertion portion and the third insertion portion are away from each other are freely switchable; and a cooperation mechanism for connecting the first movable joint portion and the second movable joint portion with each other in a manner such that when the first insertion portion is made to approach or made away from the second insertion portion so as to vary a distance between the axes of the first insertion portion and the second insertion portion, a distance between the axes of the second insertion portion and the third insertion portion also varies in accordance with the movement of the first insertion portion and the second insertion portion.

PREFERRED EMBODIMENTS OF THE INVENTION

First Embodiment

Figure 1:
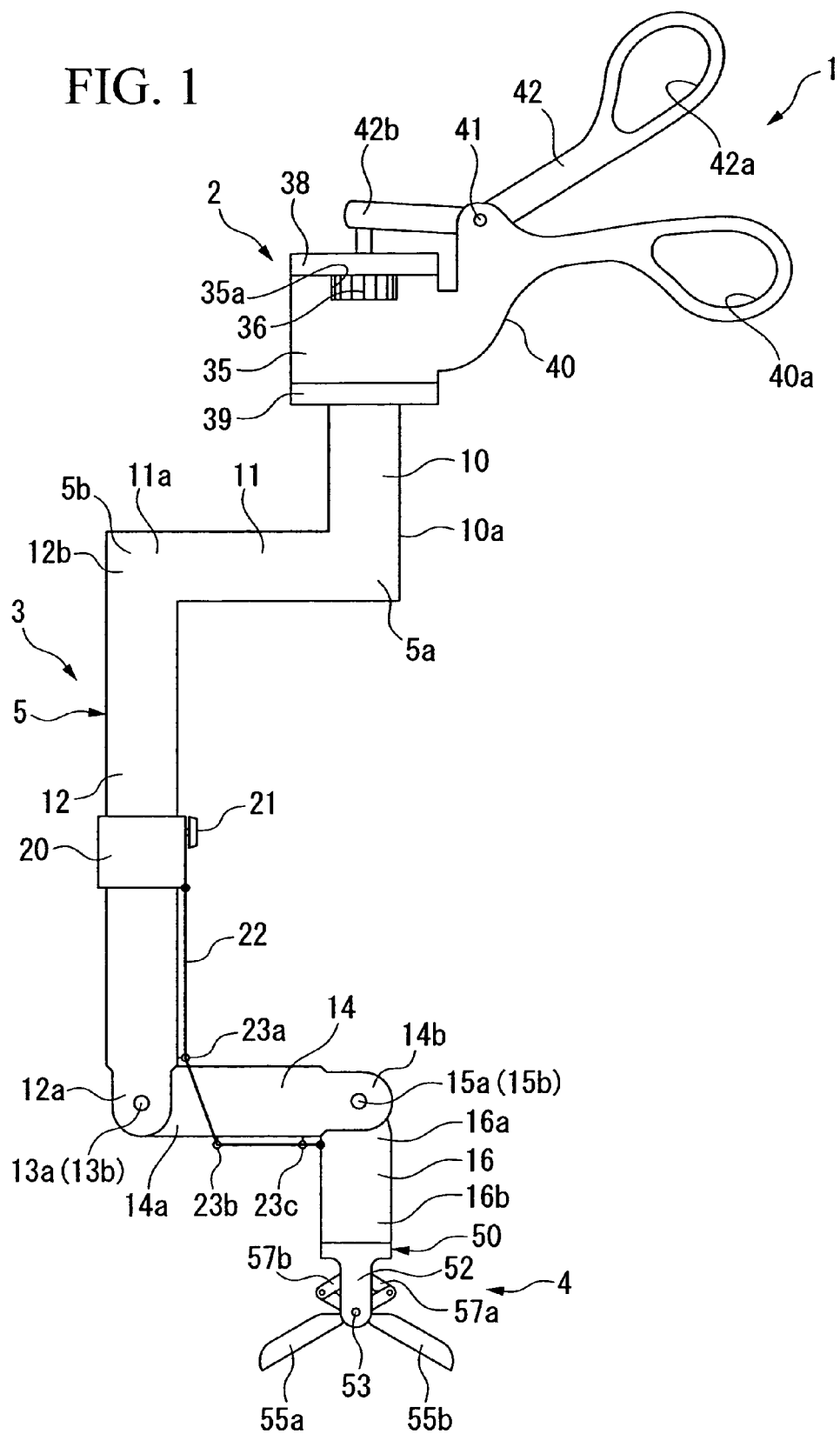
FIG. 1 is a diagram showing the structure of a surgical treatment tool as an embodiment of the instrument for the endoscope.

FIG. 1 shows a surgical treatment tool as a first embodiment of the instrument for the endoscope.

A surgical treatment tool 1 has an operation section 2 operated by an operator, an insertion section 3 which extends from the operation section 2, and a treatment section 4 provided at the head of the insertion section 3 so as to perform treatment on a living body.

The insertion section 3 has an outer pipe 5 formed by bending a metal pipe member having an outer diameter of 3 to 15 mm. The outer pipe 5 has a first insertion portion 10 connected to the operation section 2. The first insertion portion 10 extends along the axis of the operation section 2. A head portion 10a (a far end portion) of the first insertion portion 10 forms a first bent portion 5a which is substantially perpendicularly bent. From the first bent portion 5a, a first offset portion 11 extends in a direction perpendicular to the axis of the first insertion portion 10. A head portion 11a (a far end portion) of the first offset portion 11 forms a second bent portion 5b which is substantially perpendicularly bent. From the second bent portion 5b, a second insertion portion 12 extends parallel to the axis of the first insertion portion 10.

Pins 13a and 13b pass through a head portion 12a of the second insertion portion 12 (i.e., a head portion of the outer pipe 5) in a direction perpendicular to the longitudinal axis of the second insertion portion 12. The pins 13a and 13b are also perpendicular to the first offset portion 11. To the head portion 12a of the second insertion portion 12, a base portion 14a (a near end portion) of a second offset portion 14 made of a metal pipe member having an outer diameter of 3 to 15 mm is attached via the pins 13a and 13b in a freely rotatable form. Pins 15a and 15b pass through a head portion 14b (a far end portion) of the second offset portion 14, in a direction perpendicular to the longitudinal axis of the second offset portion 14. The pins 15a and 15b are arranged parallel to the pins 13a and 13b. To the head portion 14b of the second offset portion 14, a base portion 16a (a near end portion) of a third insertion portion 16 made of a metal pipe member having an outer diameter of 3 to 15 mm is attached via the pins 15a and 15b in a freely rotatable form.

The length of the second offset portion 14 is substantially the same as the length of the first offset portion 11. The head portion 12a of the second insertion portion 12 contacts the base portion 14a of the second offset portion 14 in a manner such that the longitudinal axes of the second insertion portion 12 and the second offset portion 14 are at 90 degrees. In this arrangement, the second offset portion 14 is parallel to the first offset portion 11. The second offset portion 14 contacts the third insertion portion 16 in a manner such that the longitudinal axes of the two portions are at degrees. In this arrangement, the third insertion portion 16 is parallel to the first insertion portion 10 and the second insertion portion 12. In addition, the third insertion portion 16 and the first insertion portion 10 are coaxial.

The length of the second insertion portion 12 of the outer pipe 5 is sufficiently longer than the length of a trocar (as a passage for connecting the inside and the outside of a coelom) which is provided at a coelom. In a state in which the surgical treatment tool 1 is inserted into the trocar, the insertion section can be advanced or withdrawn in the length direction of the trocar. Instead of the trocar, an assistant sleeve may be used as the passage for connecting the inside and the outside of the coelom.

A ring 20 is attached to the outer periphery of the second insertion portion 12 where the ring can slide in the longitudinal axial direction of the insertion portion 12. In the outer periphery of the ring 20, a threaded hole (not shown) is provided. The ring 20 can be fixed to a desired position of the outer pipe 5 by screwing a fastening screw 21 into the threaded hole. To the ring 20, an end of an angle wire 22 is fastened. The angle wire 22 passes through (i) a wire guide 23a provided at a side of the head portion 12a of the second insertion portion 12 toward the second offset portion 14, (ii) a wire guide 23b provided at a side of the base portion 14a of the second offset portion 14 opposite a side toward the first offset portion 11, and (iii) a wire guide 23c provided at the head portion 14b of the second offset portion 14 and at a position facing the third insertion portion 16, in turn, and is then fastened to a side of a base portion of the third insertion portion 16, which faces the second offset portion 14.

Figure 2:
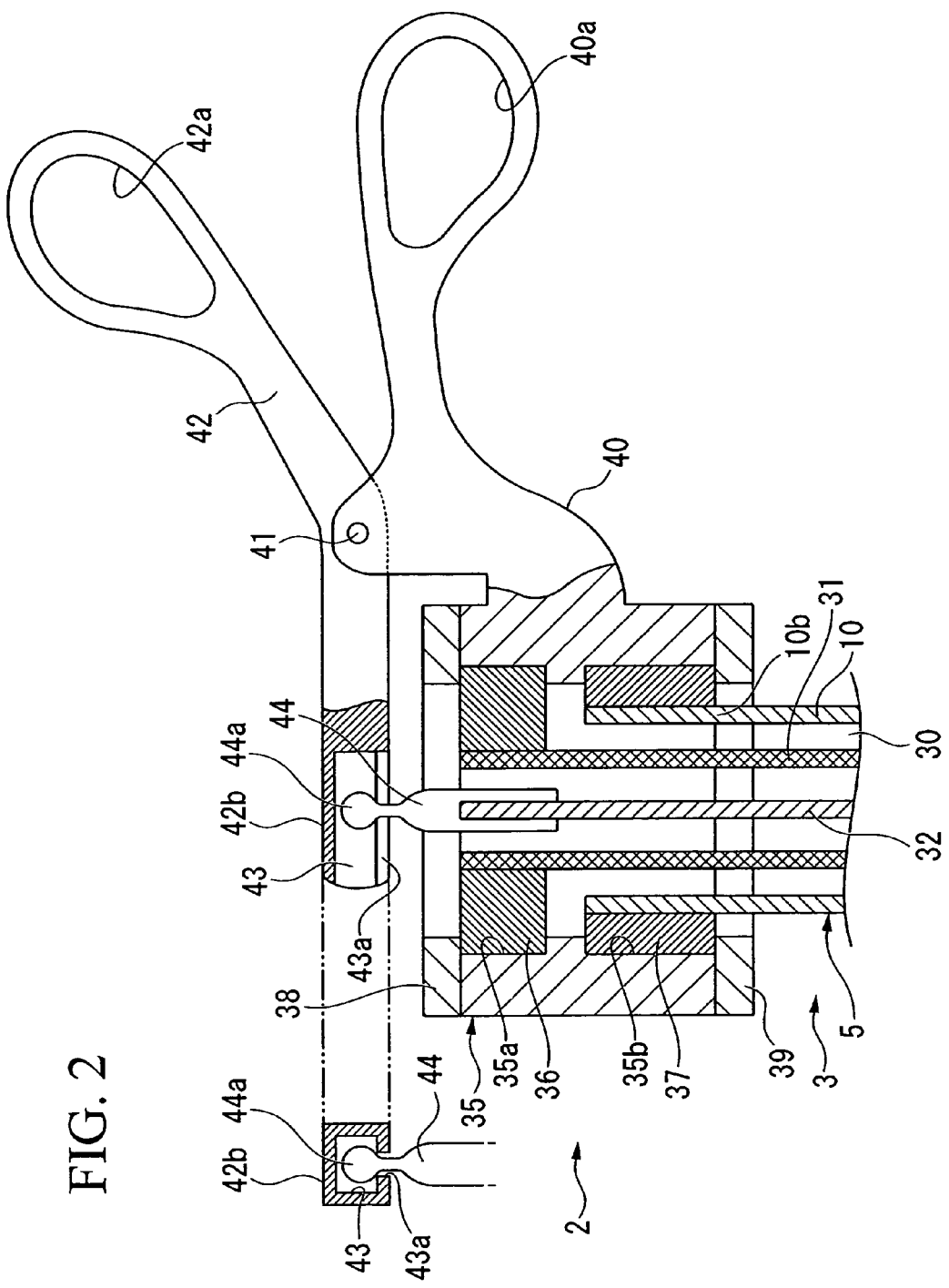
FIG. 2 is a sectional view showing the structure of an operation section.
Figure 3:
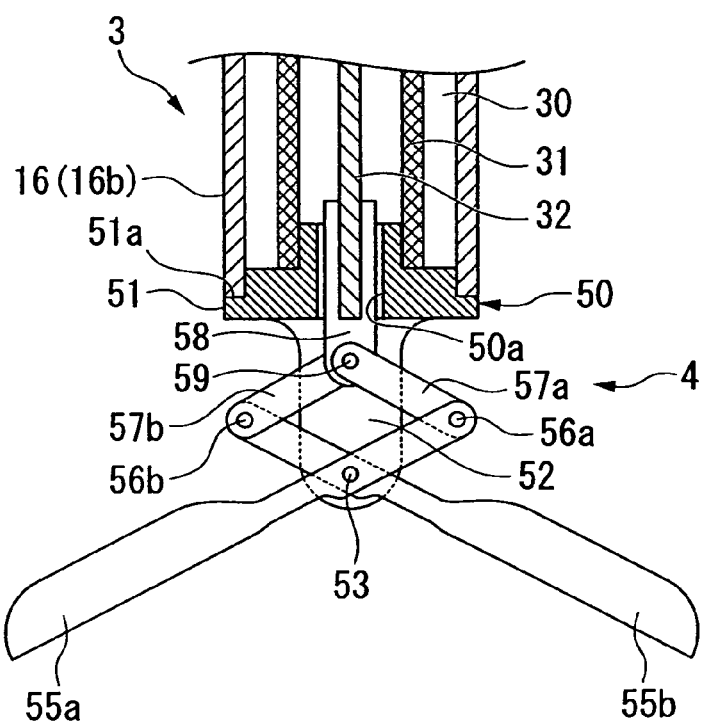
FIG. 3 is a sectional view showing the structure of a treatment section.

As shown in FIGS. 2 and 3, in the insertion section 3, a working channel 30 (an inner hole) is formed from the inside of the outer pipe 5 to the inside of the third insertion portion 16. In the channel 30, a coil 31 (i.e., a driving force transmitting device) is inserted in a freely rotatable form. The coil 31 is flexible and made of metal which can transmit torque. Inside the coil 31, a metal wire 32 (i.e., a driving force transmitting device) is inserted in a manner such that the wire 32 can freely advance or withdraw with respect to the coil 31.

A base end side of the coil 31 is inserted into a main body 35 of the operation section 2. As shown in FIGS. 1 and 2, the main body 35 has a cylindrical form, and circular grooves 35a and 35b are respectively formed at head and base sides of the inner periphery of the main body 35. Rings 36 and 37 are respectively inserted into the grooves 35a and 35b. To the inner periphery of the ring 36, an outer peripheral face of a base portion of the coil 31 is fastened by a method such as brazing, welding, or adhesion. At the base end of the main body 35, a cap member 38 is attached in a manner such that the cap member 38 pushes the ring 36. Because of the cap member 38, movement of the ring 36 in the axial direction is prevented, and a specific weight is applied to rotation of the ring 36 with respect to the main body 35. To the inner periphery of the ring 37 at the head side, an outer peripheral face of the base portion 10a (the far end portion) of the first insertion portion 10 is fastened by a method such as brazing, welding, or adhesion. At the head end of the main body 35, a cap member 39 is attached in a manner such that the cap member 39 pushes the ring 37. Because of the cap member 39, movement of the ring 37 in the axial direction is prevented, and a specific weight is applied to rotation of the ring 37 with respect to the main body 35.

A fixed handle member 40 extends directly outward from the main body 35. A hole 40a for a finger is provided at the other end of the fixed handle member 40. In the vicinity of a base (i.e., an end) of the fixed handle member 40, a center portion of a movable handle member 42 is attached via a pin 41 in a freely rotatable form. A hole 42a for a finger is provided at the other end of the movable handle member 42. An end portion 42b of the movable handle member 42 extends over the axis of the main body 35, and a specific distance is secured between the end portion 42b and the cap member 38. A groove 43 is formed in the end portion 42b. The groove 43 has an open end 43a toward the cap member 38 and extends from the end face of the end portion 42b along the length of the movable handle member 42. The width of the open end 43a in a direction perpendicular to the length direction of the groove 43 is less than the width of the remaining portion of the groove 43. In the groove 43, a fitting member 44 is inserted through the open end 43a. A base end of the wire 32 is fastened to the fitting member 44 by a method such as brazing, welding, or adhesion. In the fitting member 44, a spherical portion 44a is provided which enters the groove 43. The diameter of the spherical portion 44a is larger than the narrowed width of the groove 43. The fitting member 44 can freely slide along the groove 43. Owing to the fit spherical portion 44a, the fitting member 44 cannot be detached in a direction along the axis of the fitting member 44 (i.e., in the axial direction).

Figure 4:
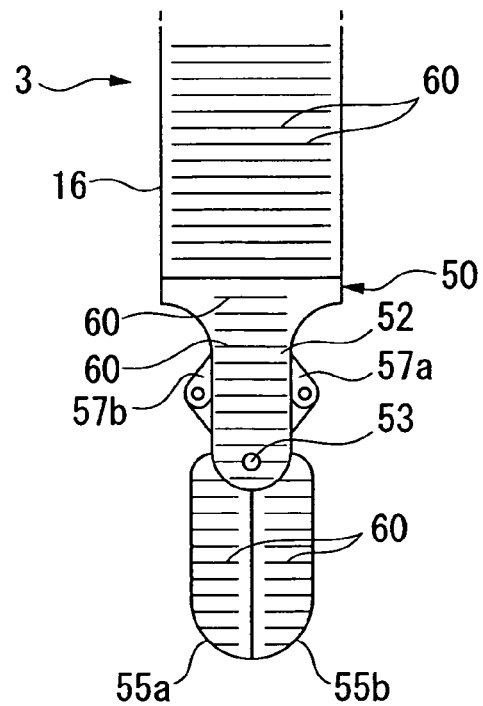
FIG. 4 is a diagram showing a head portion of an insertion section and divisions of a scale provided in the treatment section.
Figure 5:
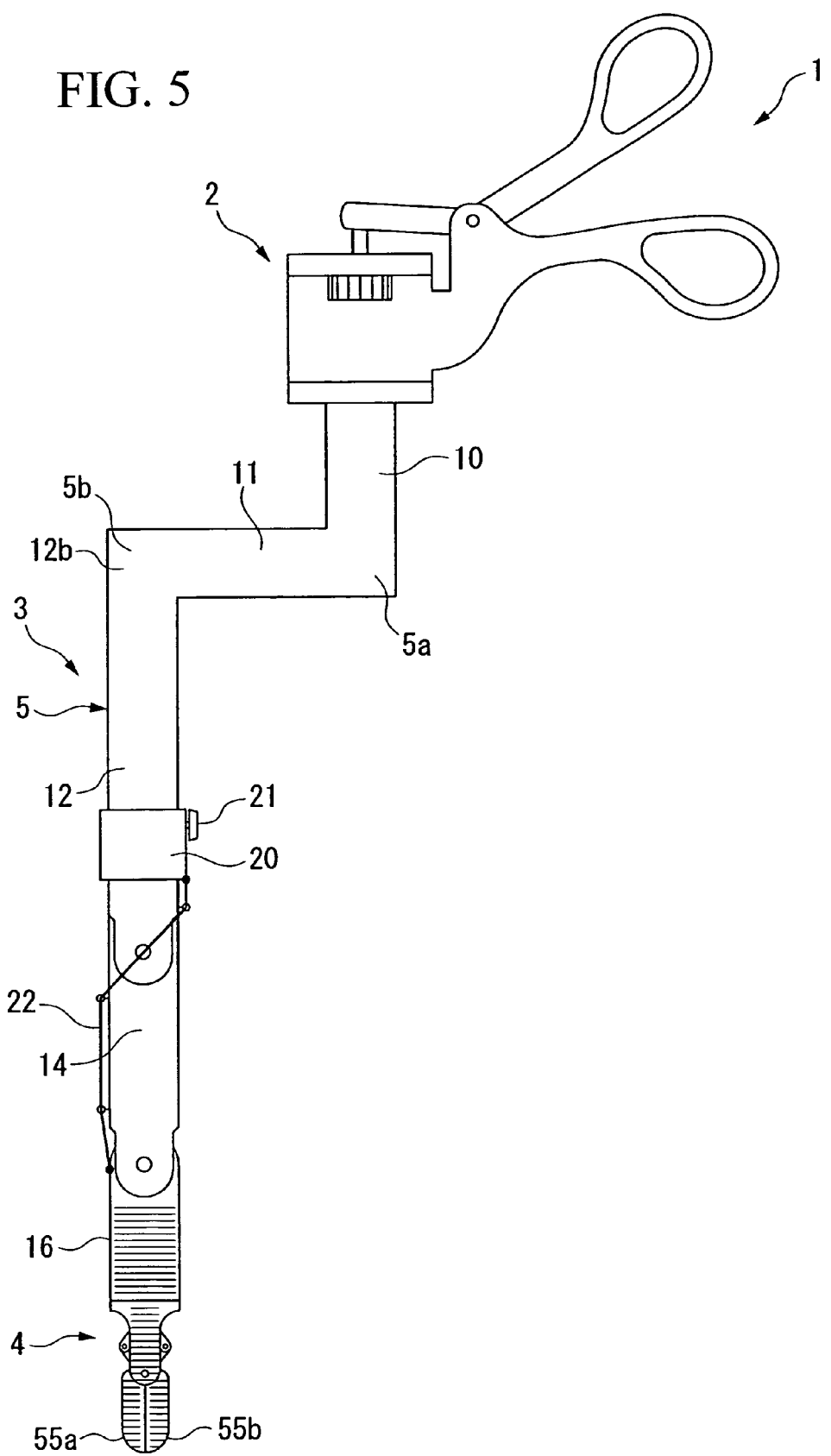
FIG. 5 is a diagram showing a state in which the head side of the insertion section is linearly arranged.

As shown in FIG. 3, a housing member 50 is attached to the head side of the coil 31 by a method such as brazing, welding, or adhesion. A through hole 50a is formed at the center of the housing member 50. The housing member 50 is inserted from the head side of the third insertion portion 16 and is fit to an inner peripheral face of the third insertion portion 16 in a freely rotatable form. In addition, an end face 51a of a flange portion 51 of the housing member 50 contacts an end face of the head portion 16b (the far end portion) of the third insertion portion 16. From the head portion of the housing member 50, a pair of supports 52 extend in a manner such that the supports 52 are arranged parallel to each other along their axes and thus face each other, and a specific gap is provided between the supports 52. A pin 53 passes through the supports 52 in a direction perpendicular to their axes. The pin 53 passes through a pair of clipping members 55a and 55b which are overlapped in a direction along the axis of the pin 53. The clipping members 55a and 55b are each supported via the pin 53 by the housing member 50 in a freely rotatable form, and head sides of the clipping members 55a and 55b from the center portion where the pin 53 is provided can clip a portion of a living body. To base end sides of the clipping members 55a and 55b from the position of the pin 53, base end portions of the link members 57a and 57b are respectively coupled via pins 56a and 56b in a freely rotatable form. A head portion of a wire joint member 58 is held between base end portions of the link members 57a and 57b, which are coupled to the wire joint member 58 via a pin 59 in a freely rotatable form. The wire joint member 58 is fastened to an end of the wire 32 by a method such as brazing. As shown in FIG. 4, divisions 60 of a scale are provided on the surfaces of the pair of the clipping members 55a and 55b, the housing member 50, and the third insertion portion 16.

The operation of the present embodiment will be explained below.

First, the surgical treatment tool 1 is inserted into a trocar provided through a body wall of a patient. In the insertion process, the second insertion portion 12 of the outer pipe 5, the second offset portion 14, and the third insertion portion 16 are substantially linearly arranged, and the third insertion portion 16, the second offset portion 14, and the second insertion portion 12 are inserted in turn from the trocar.

In treatment, the ring 20 is slid toward a base end portion 12b (a far end portion corresponding to the second bent portion 5b) of the second insertion portion 12. The angle wire 22 fastened to the ring 20 then pulls a head ring 9 and the second offset portion 14 in turn. The third insertion portion 16 rotates around the pins 15a and 15b until the third insertion portion 16 contacts the head portion of the second offset portion 14 and the third insertion portion 16 and the second offset portion 14 are at 90 degrees to each other. The second offset portion 14 rotates around the pins 13a and 13b until the second offset portion 14 contacts the head portion 12a of the second insertion portion 12 and the second offset portion 14 and the second insertion portion 12 form a 90 degree angle. When the fastening screw 21 is screwed and fastened, the ring 20 is fastened to the second insertion portion 12, and the third insertion portion 16 is fastened to the second offset portion 14, and the second offset portion 14 is fastened to the second insertion portion 12.

Figure 6:
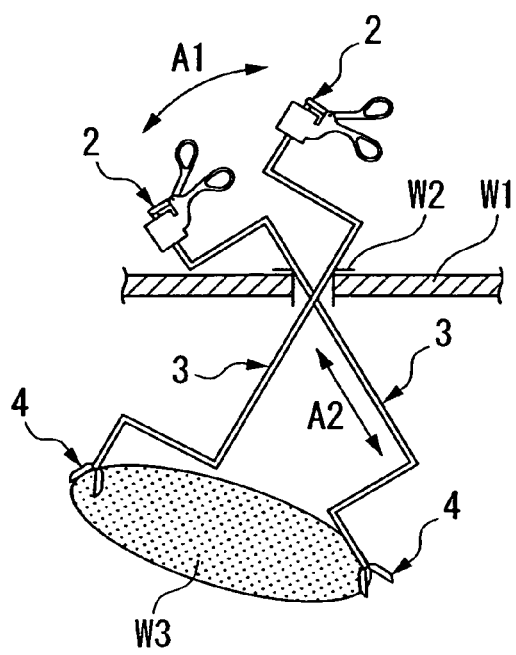
FIG. 6 is a diagram explaining a method of using the surgical treatment tool.
Figure 7:
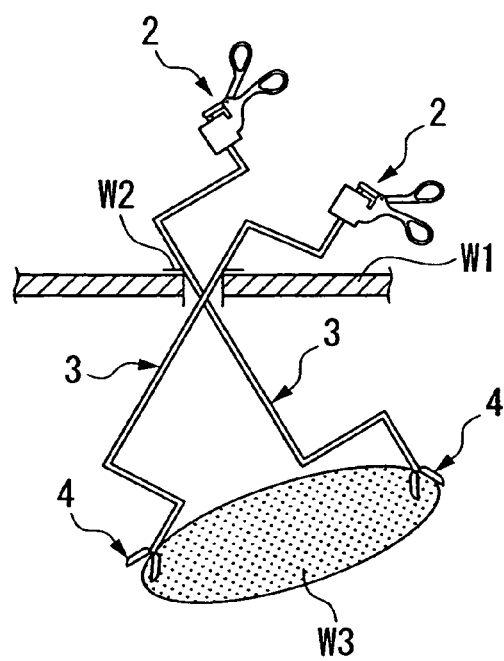
FIG. 7 is a diagram explaining a method of using the surgical treatment tool.

As shown in FIG. 6, the treatment section 4 is inserted toward a treatment target part W3 through a trocar W2 provided at a body wall W1. In this state, the head portion of the surgical treatment tool 1 can be positioned at a desired position by appropriately moving the surgical treatment tool 1 in a direction A1 for angling the surgical treatment tool 1 with respect to the longitudinal axial direction of the trocar W2 or a direction A2 for advancing or withdrawing the surgical treatment tool 1 in a direction along the axis of the trocar W2. In addition, as shown in FIGS. 6 and 7, when the head portion from the first bent portion 5a of the outer pipe 5 inserted in the trocar W2 is rotated around the longitudinal axial direction of the trocar W2, the head portion of the surgical treatment tool 1 can be arranged at various positions, so that the head portion can be positioned in a wider area.

When the fixed handle member 40 and the movable handle member 42 are grasped and brought close to each other, the end portion 42b of the movable handle member 42 leaves the main body 35, and the fitting member 44, fit to the groove 43 of the end portion 42, is pulled toward the base end side in the axial direction. Accordingly, the wire 32 is also pulled toward the base end side, and the wire joint member 58 attached to the head end of the wire 32 pulls the link members 57a and 57b. Then the pair of clipping members 55a and 55b coupled to the link members 57a and 57b rotate around the pin 53, and the head portions of the clipping members 55a and 55b approach each other and close. When the operation section 3 is operated so as to open the fixed handle member 40 and the movable handle member 42, the end portion 43 moves toward the cap member 38. Accordingly, the wire 32 is pushed via the fitting member 44, and the head portions of the clipping members 55a and 55b are separated and opened.

When the fixed handle member 40 is grasped and the main body 35 is rotated with respect to the outer pipe 5 around the axis of the first insertion portion 10, the ring 36, having a specific frictional force for the main body 35, rotates together with the main body 35. The coil 31 is fastened to the ring 36, and the housing 50 is fastened to the head portion of the coil 31. Therefore, rotation of the ring 36 is transmitted by the coil 31 to the housing 50 at the head side, and the pair of the clipping members 55a and 55b supported by the housing 50 rotates around the axis of the third insertion portion 16. Accordingly, in response to the rotation of the main body 35 around the axis of the fixed handle member 40, the pair of the clipping members 55a and 55b rotate around the axis. In addition, when the ring 36 is rotated with respect to the main body 35 against the specific friction force, for example, by applying a finger to a side face of the ring 36 exposed through a window 35a of the main body 35 (see FIG. 1), the rotation of the ring 36 is transmitted via the coil 31 to the head treatment section 4. Accordingly, the pair of the clipping members 55a and 55b can be rotated around the axis without changing the position of the fixed handle member 40.

Figure 8:
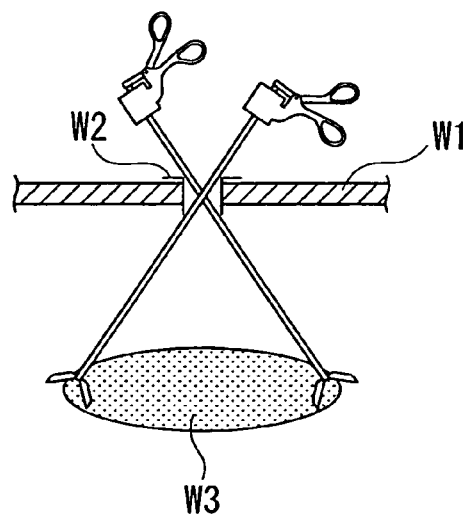
FIG. 8 is a diagram explaining a method of using a conventional surgical treatment tool.

In the conventional technique, the area where treatment can be performed through a single trocar W2 is as shown in FIG. 8. In contrast, is the present embodiment, the area where treatment can be performed through a single trocar W2 is wider as shown in FIGS. 6 and 7. Therefore, a smaller number of trocars W2 is necessary in a surgical operation. A time period necessary for inserting trocars W2 in the body wall W1 and a time period necessary for pulling out the treatment tool from a trocar W2 and inserting the tool through another trocar W2 can be reduced, thereby reducing a time necessary for each surgical operation and also reducing damage to the patient.

In addition, the treatment section 4 and the operation section 2 are coaxially arranged; thus, it is easy for the operator to intuitively know the position of the treatment section 4, and the operator can easily operate the treatment tool. Accordingly, quick and reliable treatment can be performed.

Furthermore, divisions 60 of a scale are provided in a head portion of the tool; thus, it is easy for the operator to visually determine the depth. In particular, in an endoscope operation performed with watching two-dimensional images, a safer and more reliable operation is possible.

Figure 9:
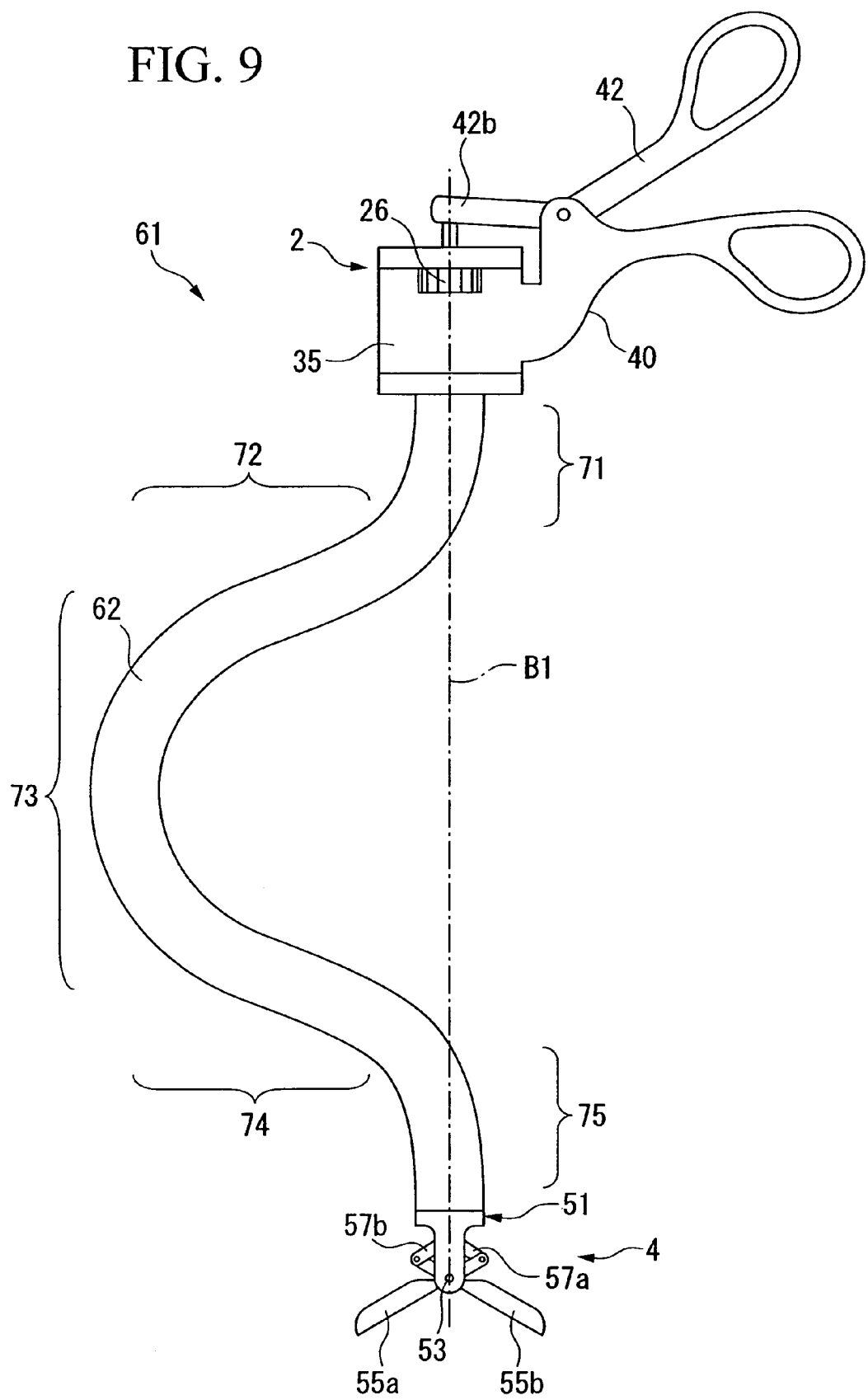
FIG. 9 is a diagram showing a variation of the insertion section.

FIG. 9 shows a variation. A shown surgical treatment tool 61 has a bent pipe 62 having a specific curvature, which can be inserted into a trocar. The bent pipe 62 has a first insertion portion 71 whose base end portion is connected to the operation section 2. The axis of the first insertion portion 71 is aligned to the axis B1 of the operation section 2. From a head portion of the first insertion portion 71, a first offset portion 72 extends, where the portions 71 and 72 form a single body. The first offset portion 72 is bent so as to leave the axis B1. A portion furthest from the axis B1 functions as a second insertion portion 73 joined to the first offset portion 72. The second insertion portion 73 is bent while generally extending in a direction substantially parallel to the axis B1. That is, the second insertion portion 73 has an element parallel to the axis B1. At the head of the second insertion portion 73, a second offset portion 74 is provided, which is bent toward the axis B1 and has a substantially symmetrical form with respect to the first offset portion 72. At the head of the second offset portion 74, a third insertion portion 75 is provided, which extends substantially coaxially to the axis B1 so as to further leave the operation section 2. The treatment section 4 is attached to the third insertion portion 75. Inside the bent pipe 62, the coil 31 and the wire 32 pass through in a freely rotatable form. In accordance with the surgical treatment tool 61, functions and effects similar to those described above can be obtained.

Second Embodiment

Figure 10:
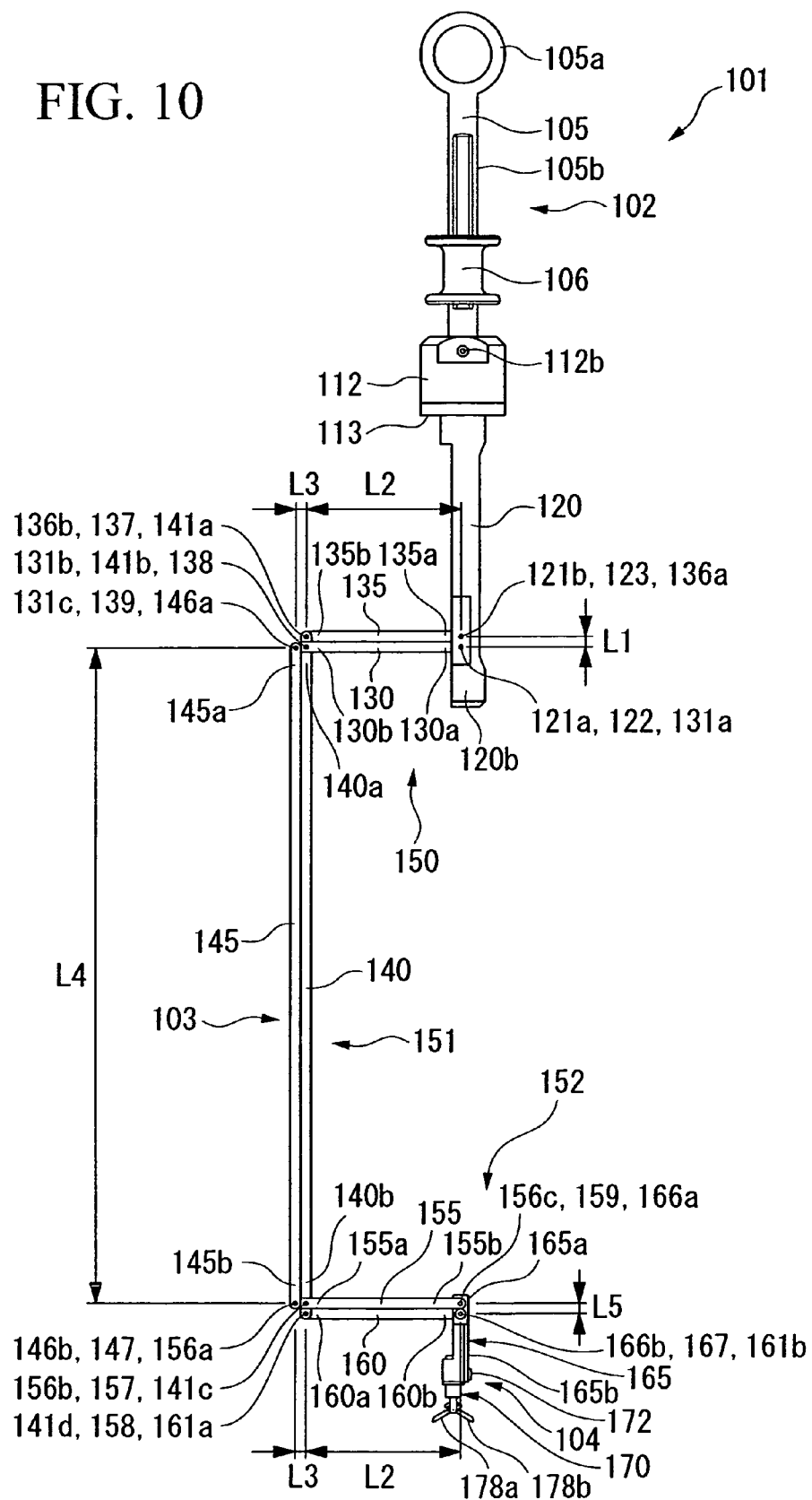
FIG. 10 is a diagram showing the structure of a surgical treatment tool as the instrument for the endoscope.

FIG. 10 shows a surgical treatment tool as a second embodiment of the instrument for the endoscope.

In a surgical treatment tool 101, an insertion section 103 extends from an operation section 101, and a treatment section 104 is provided at the head of the insertion section 103.

Figure 11:
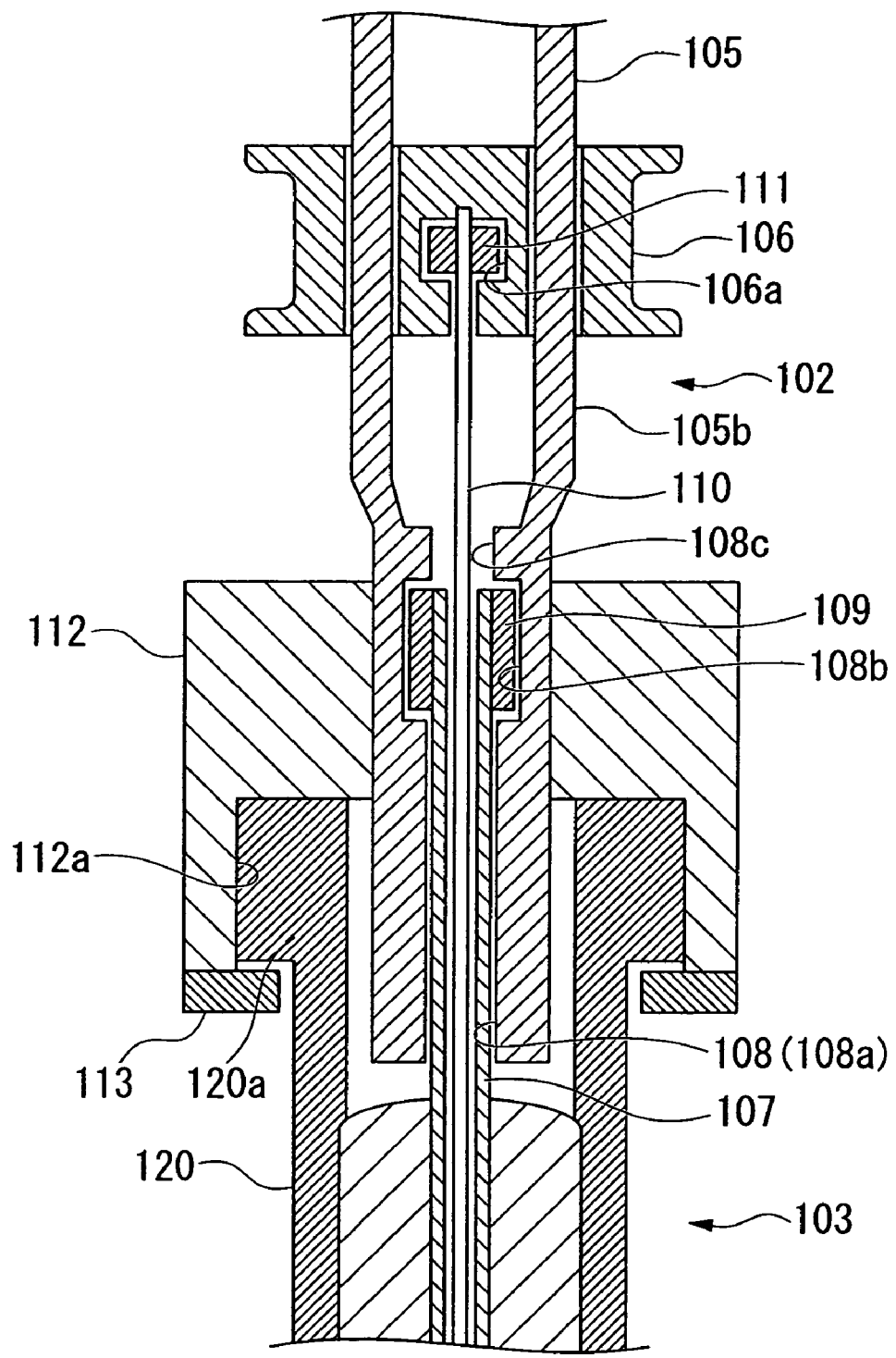
FIG. 11 is a sectional view showing the structure of an operation section.

As shown in FIGS. 10 and 11, the operation section 102 has a fixed handle member 105 and a movable handle member 106 which can slide along the fixed handle member 105 (in the longitudinal axial direction). The fixed handle member 105 has a ring 105a to be caught by a finger, at the base side of the fixed handle member 105. In an intermediate portion of the fixed handle member 105, a rail portion 105b is provided, which has a long hole formed along the length of the rail portion 105b. The movable handle member 106 slides along the rail portion 105b. As shown in FIG. 11, on a head side of the fixed handle member 105, a U-shaped groove 108 is provided for containing a coil 107 (i.e., a driving force transmitting member). The groove 108 has a first section 108a at the head side, which can accept the outer diameter of the coil 107, a second section 108b which is larger than the first section 10ba, and a third section 108c for connecting the second section 108b and the rail portion 105b. To the second section 108b, a coil holding member 109, attached to a base end of the coil 107, is pressed and fastened. The coil holding member 109 is fastened to the base end of the coil 107 by a method such as autosplice processing or brazing. A wire 110 (i.e., a driving force transmitting member) passes through the third section 108c. To the base end of the wire 110, a wire holding member 111 is fastened by a method such as clamping or brazing. The wire holding member 111 is contained in a groove 106a provided at a center of the movable handle member 106. The grooves 108 and 106a are closed by caps (not shown) after the coil 107 and the wire 110 are respectively inserted.

As shown in FIG. 10, to a head portion of the fixed handle member 105, a cylindrical handle fastening member 112 is coaxially positioned and fastened by using a screw 112b. As shown in FIG. 11, a head portion of the handle fastening member 112 has a hole 112a which fits an outer periphery of a flange portion 120a provided in a base end (near end) portion of a first insertion portion 120. A ring-shaped cap member 113 is attached to an end face on the head side of the handle fastening member 112, thereby restricting movement of the first insertion portion 120 along the axis. The operating section 102 is fixed to the first insertion portion 120 in the longitudinal axial direction; however, the operating section 102 can freely rotate with respect to the first insertion portion 120 around the axis.

A head portion 120b (a far end portion) of the first insertion portion 120 has a hole 121a which opens in a direction perpendicular to the axis of the first insertion portion 120. Another hole 121b is also provided, which is closer to the base end side, and a specific distance L1 is secured between the holes 121a and 121b. Pins 122 and 123 are respectively inserted into the holes 121a and 121b. The pin 122 passes through a hole 131a of a base end portion 130a of a link member 130 (i.e., a first offset portion), so that the base end portion 130a of the link member 130 is attached to the head portion 120b of the first insertion portion 120 via the pin 122 in a freely rotatable form. The pin 123 passes through a hole 136a of a base end portion 135a of a link member 135, so that the base end portion 135a of the link member 135 is attached to the head portion 120b of the first insertion portion 120 via the pin 123 in a freely rotatable form. The link members 130 and 135 are arranged parallel to each other.

A hole 131b is formed in a head portion 130b of the link member 130, and a specific distance L2 is secured between the holes 131a and 131b along the length of the link member 130. At a position away from the hole 131b by a further distance L3 in the same direction, another hole 131c is formed. Similarly, in a head portion 135b of the link member 135, a hole 136b is provided so that the specific distance L2 is secured between the holes 136a and 136b.

A pin 137 is inserted into the hole 136b. The pin 137 is also inserted into a hole 141a provided in a base end portion 140a of a link member 140, so that the base end portion 140a of the link member 140 is coupled to the head portion 135b of the link member 135 via the pin 137 in a freely rotatable form. The link member 140 has a hole 141b at a position away from the hole 141a by a distance L1 toward the other end side. A pin 138 is inserted into the hole 141b. The pin 138 is also inserted into the hole 131b of the link member 130 so that the head portion 130b of the link member 130 is coupled to the base end portion 140a of the link member 140 via the pin 138 in a freely rotatable form.

Accordingly, a parallel link structure 150 is formed by the first insertion portion 120 and the link members 130, 135, and 140, that is, by four link members.

A pin 139 is inserted into the hole 131c of the link member 130. The pin 139 is also inserted into a hole 146a formed in a base end portion 145a of a link member 145, so that the base end portion 145a of the link member 145 is coupled to the head portion 130b of the link member 130 via the pin 139 in a freely rotatable form. The link member 145 has a hole 146b at a position away from the hole 146a by a distance L4 toward a head portion 145b. The distance L4 is sufficiently larger than the distance of a trocar W2 (see FIG. 13) into which the surgical treatment tool 101 is inserted, so that the surgical treatment tool 101 can advance or withdraw through the trocar W2 while the surgical treatment tool is inserted in the trocar W2.

A pin 147 is inserted into the hole 146b. The pin 147 is also inserted into a hole 156a provided in a base end portion 155a of a link member 155, so that the base end portion 155a of the link member 155 is coupled to the head portion 145b of the link member 145 via the pin 147 in a freely rotatable form. The link member 155 has a hole 156b at a position away from the hole 156a by the distance L3 toward the head end side. A pin 157 is inserted into the hole 156b. The pin 157 is also inserted into a hole 141c formed in a head portion 140b of the link member 140. The hole 141c is formed at a position away from the hole 141b by the distance L4 toward the other end side of the link member 140. The head portion 140b of the link member 140 is coupled to the base end portion 155a of the link member 155 via the pin 157 in a freely rotatable form.

Accordingly, a parallel link structure 151 is formed by the link members 130, 140, 145, and 155.

The link member 140 has a hole 141d at a position away from the hole 141c by a distance L5 toward the head portion 140b. A pin 158 is inserted into the hole 141d. The pin 158 is also inserted into a hole 161a provided in a base end portion 160a of a link member 160. The base end portion 160a of the link member 160 is coupled to the head portion 140b of the link member 140 via the pin 158 in a freely rotatable form.

The link member 155 has a hole 156c at a position away from the hole 156b by the distance L2 toward the head portion 155b. A pin 159 is inserted into the hole 156c. The pin 159 is also inserted into a hole 166a provided in a base end portion 165a of a head link member 165. The base end portion 165a of the head link member 165 is coupled to the head portion 155b of the link member 155 via the pin 159 in a freely rotatable form. The head link member 165 has a hole 166b at a position away from the hole 166a by the distance L5 toward the other end side. A pin 167 is inserted into the hole 166b. The pin 167 is also inserted into a hole 161b which is formed in the link member 160 at a position away from the hole 161a by the distance L2 toward the head portion 160b. The head portion 160b of the link member 160 is coupled to the base end portion 165a of the head link member 165 via the pin 167 in a freely rotatable form.

Accordingly, a parallel link structure 152 is formed by the link members 140, 155, and 160, and the head link member 165.

Figure 12:
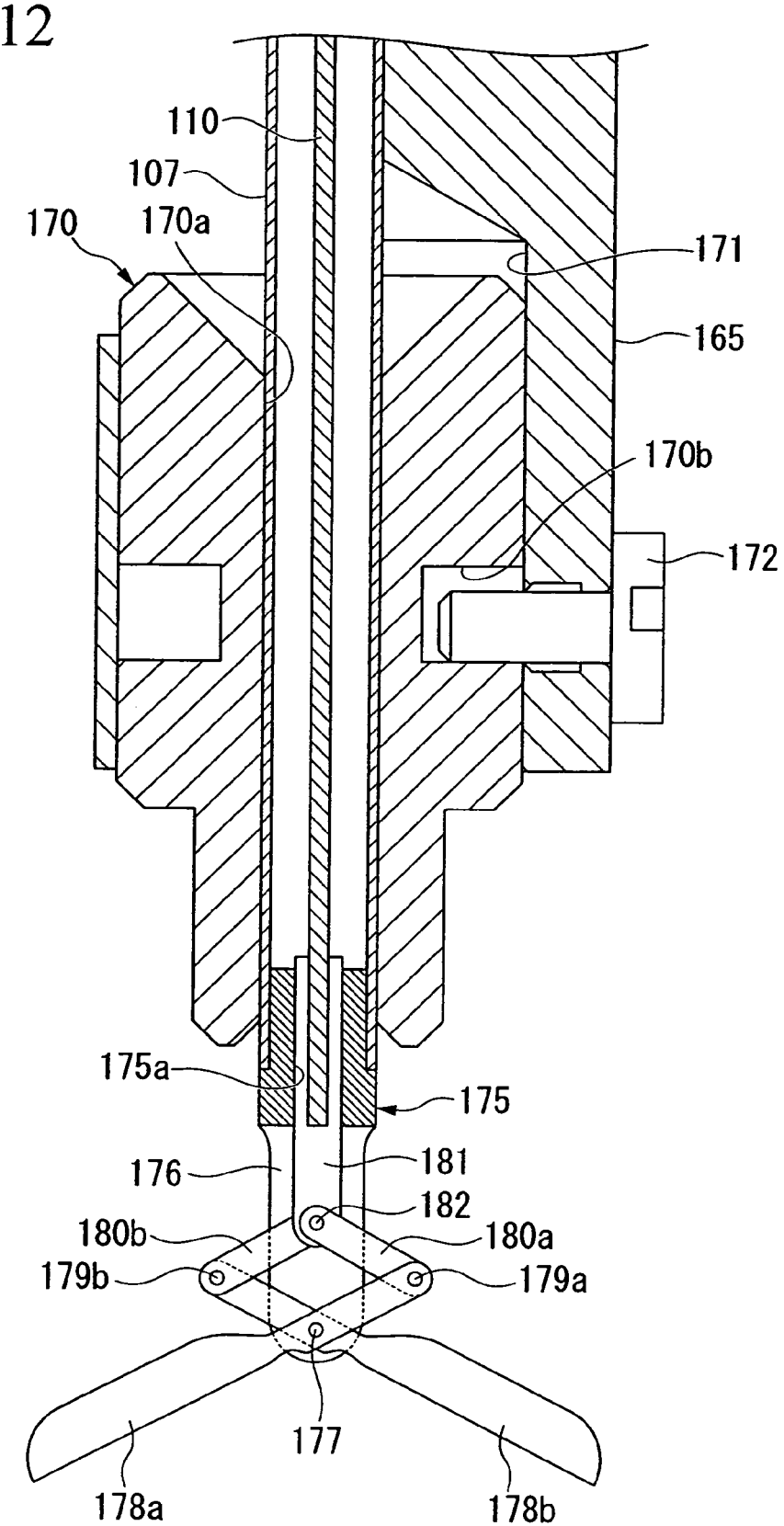
FIG. 12 is a sectional view showing the structure of a treatment section.

As shown in FIG. 12, in a head portion 165b of the head link member 165, a hole 171 is formed so as to contain a cylindrical coil holding member 170 which is fit to the hole 171. The coil holding member 170 has a through hole 170a for accepting the outer diameter of the coil 107. A head portion of the coil 107 is inserted and fixed to the through hole 170a. The coil holding member 170 has a smaller-diameter portion 170b having a smaller outer diameter at substantially the center in the length direction of the member 170. A pin 172 fastened to the head link member 165 is received by the smaller-diameter portion 170b. In accordance with the above structure, the coil holding member 170 and the coil 107 are fastened to the head link member 165 in the longitudinal axial direction; however, they are freely rotatable with respect to the head link member 165 around the longitudinal axial direction.

To the head of the coil 107, a head housing member 175 is fastened by a method such as brazing, welding, or adhesion. A through hole 175a is formed in a center portion of the head housing member 175. From the head of the head housing member 175, a pair of supports 176 extends, to which a pin 177 is inserted in a direction perpendicular to the axes of the supports. A center portion of a pair of clipping members 178a and 178b is supported by the pin 177 in a freely rotatable form. Ends of link members 180a and 180b are respectively attached to base ends of the clipping members 178a and 178b via the pins 179a and 179b. A head portion of a wire joint member 181 is held between the other ends of the link members 180a and 180b which are coupled to each other by a pin 182 in a freely rotatable form. The wire joint member 181 is fastened to an end of the wire 110 by a method such as brazing. A rotating operation of the operation section 102 is transmitted via the coil 107 to the treatment section 104. In addition, an opening and closing operation of the operation section 102 is transmitted to the treatment section 104 by the wire passing through the coil 107.

In the insertion section 103, two link members 130 and 135 form the first offset portion extending away from the axis of the operation section 102. Two link members 140 and 145 form the second insertion portion. Two link members 155 and 160 form the second offset portion. The head link member 165 functions as the third insertion portion.

The operation of the present embodiment will be explained below.

Figure 13:
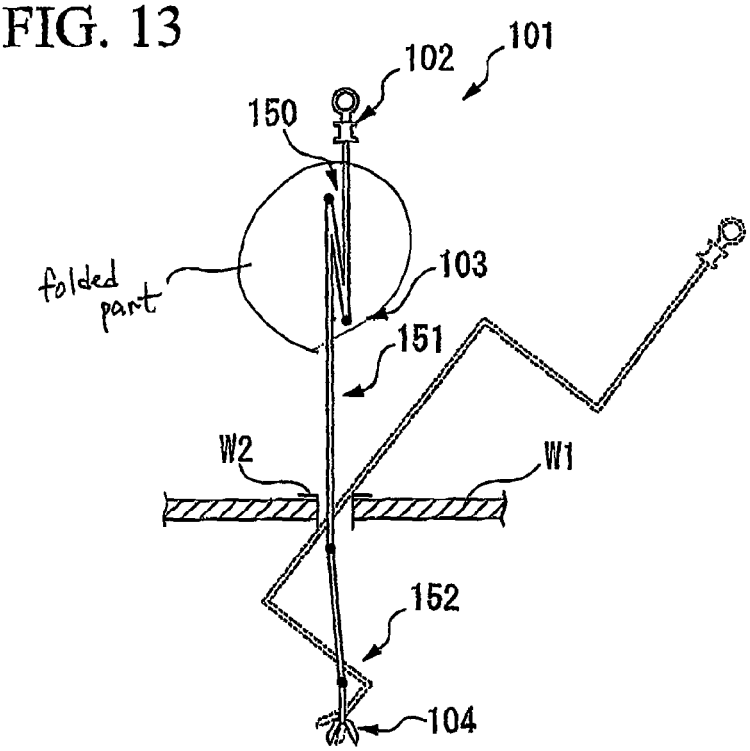
FIG. 13 is a diagram showing a method of using the surgical treatment tool and a state in which the tool is inserted in a living body.
Figure 14:
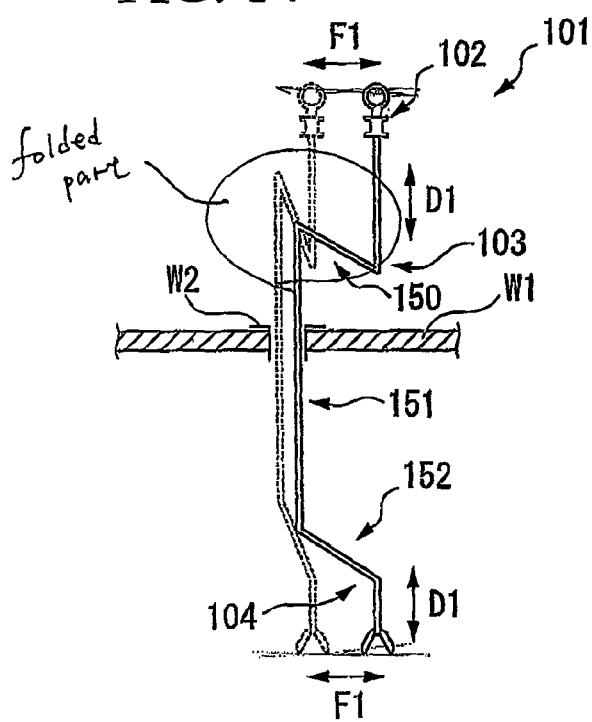
FIG. 14 is a diagram showing a method of using the surgical treatment tool and explaining an operation for changing the position of the treatment section.

The parallel link structure 150 is moved so that the first insertion portion 120 and the link member 140 are substantially linearly arranged. In the surgical treatment tool 101, in accordance with the parallel link structures 150, 151, and 152, a variation in a distance from the base end portions 140a and 145a of the link members 140 and 145 as the second insertion portion to (the longitudinal axis of) the first insertion portion 120 coincides with a variation in the distance from the head portions 140b and 145b of the link members 140 and 145 to (the longitudinal axis of) the third insertion portion 165 which is present on an extension of the axis of the first insertion portion 120. Therefore, as shown in FIG. 13, the parallel link structures 151 and 152 move together so that the elements from the treatment section 104 to the operation section 102 are substantially linearly arranged and can be inserted into the trocar W2. After the tool is inserted into the trocar W2 in this condition, the operation section 102 is operated so as to increase the distance between the first insertion portion 120 and the link member 140. As shown in FIG. 14, according to the parallel link structures 150, 151, and 152, the treatment section 104 also moves so as to depart from the link member 140, and an offset F1 from an insertion section of the trocar W2 to the treatment section 104 is changed. In addition, when the surgical treatment tool 101 is made to advance or withdraw for the trocar W2, an insertion depth D1 of the treatment section 104 in the axial direction of the trocar W2 is changed. In the above operations, a constant positional relationship is established between the treatment section 104, the first insertion portion 120, and the operation section 102.

When the operation section 102 is rotated with respect to the first insertion portion 120 around the axial direction, the rotation is transmitted to the treatment section 104 via the coil 107 fastened to the operation section 102. Therefore, in response to the rotation of the operation section 102, the treatment section 104 rotates with respect to the head link member 165 around the axis.

When the movable handle member 106 is slid along the fixed handle member 105 toward the base end side thereof, the wire 110 is pulled and the heads of the clipping members 178a and 178b of the treatment section 104 move to close. When the movable handle member 106 is slid along the fixed handle member 105 toward the head side thereof, the wire 110 is pushed inside and the heads of the clipping members 178a and 178b of the treatment section 104 move to be opened.

According to the present embodiment, regarding a single trocar W2, a wider area treatment is possible in comparison with conventional instruments. The number of trocars W2 necessary in a surgical operation can be reduced, and a time period necessary for inserting trocars W2 in a body wall W1 and a time period necessary for pulling out the treatment tool from a trocar W2 and inserting the tool through another trocar W2 can be reduced, thereby reducing a time necessary for each surgical operation and also reducing damage to the patient.

In addition, the treatment section 104 and the operation section 102 are coaxially arranged; thus, it is easy for the operator to intuitively know the position of the treatment section 104, and the operator can easily operate the treatment tool.

Figure 15:
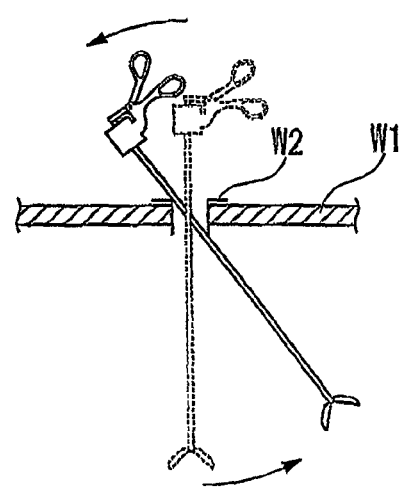
FIG. 15 is a diagram explaining a method of using a conventional surgical treatment tool.

Furthermore, in conventional instruments, as shown in FIG. 15, an operation section must be moved for a trocar W2 as a fulcrum in a direction opposite to a direction in which a treatment section is moved in a coelom. In this case, the operation is not performed intuitively, and thus considerable time is necessary for the operator to become experienced. According to the present embodiment, as shown in FIG. 14, the direction in which the operation section 102 moves coincides with that of the treatment section 104, in any case of vertical, right-left, or front-back movement. Therefore, an intuitive operation can be performed, and less time is necessary for the operator to become experienced.

In addition, in conventional instruments which are greatly restricted by the trocar W2, approach to a specific position in a coelom is permitted in a single direction depending on the position where the trocar is inserted. Therefore, it is difficult for the operator to perform the operation. In the present embodiment, as shown in FIGS. 13 and 14, the direction of approach to a specific position in a coelom can be changed by adjusting the offset amount of the treatment section 104 for the trocar W2 (in the direction perpendicular to the axis of the trocar W2), or the amount of insertion in the direction of the axis of the trocar W2. Therefore, the operation can be performed considerably easily. It is unnecessary to consciously perform the above adjustment of the offset amount or the amount of insertion. Such adjustment is possible when the operator moves the operation section 102 with a feeling as if the trocar W2 were not present. As the operation can be easily performed, treatment can be performed more safely and reliably. Therefore, a time period necessary for each surgical operation can be reduced, and both the patient and operator receive less burden.

Third Embodiment

Figure 16:
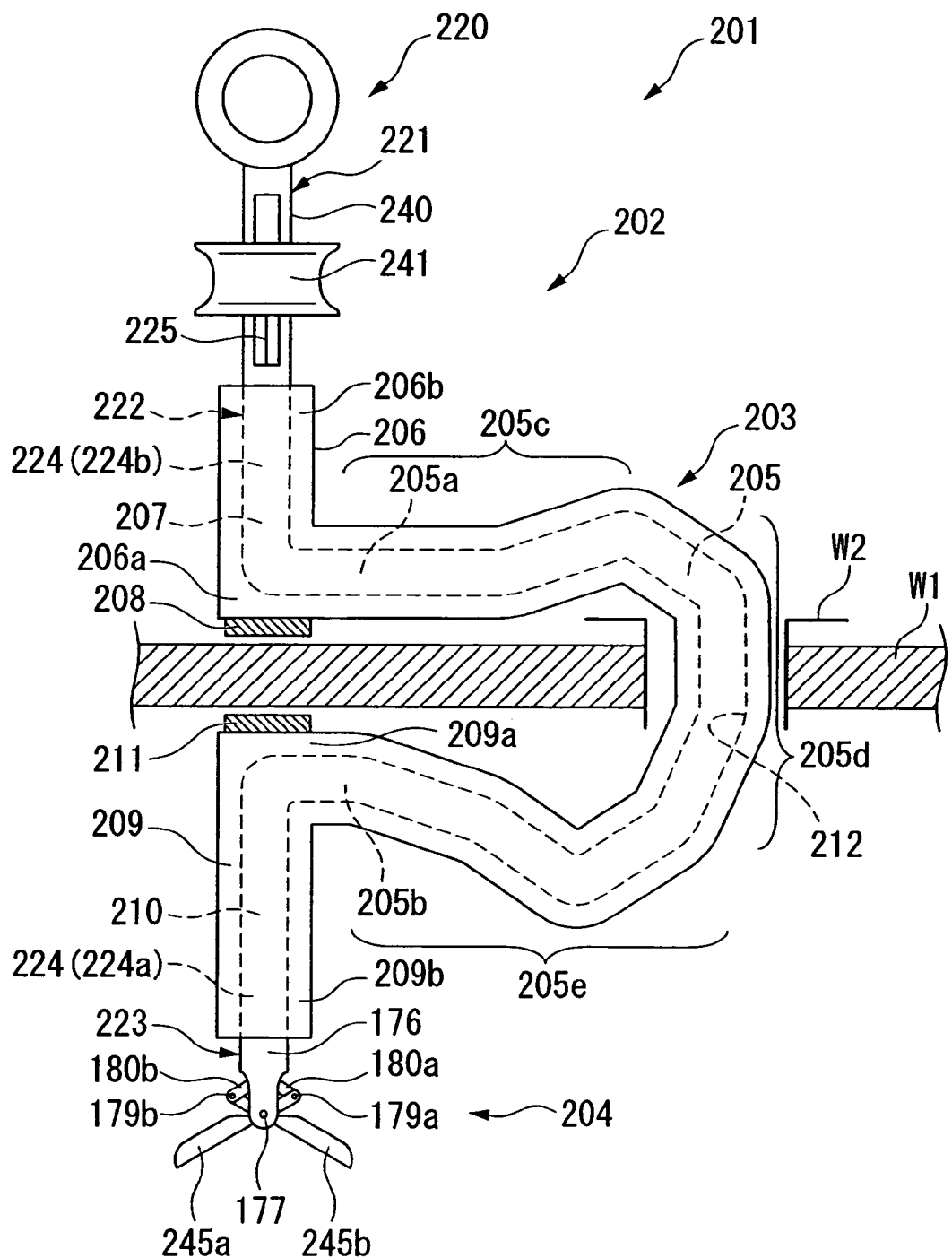
FIG. 16 is a diagram showing the structure of a surgical treatment tool as the instrument for the endoscope, and a state in which a portion of the insertion section is inserted in a living body.

FIG. 16 shows a surgical treatment tool as a third embodiment of the instrument for the endoscope.

A surgical treatment tool 201 has an insertion section 203 extending from the head of an operation section 202, and a treatment section 204 is provided at the head of the insertion section 203.

The insertion section 203 is made of a hollow pipe line 205 which is flexible and has an appropriate degree of hardness. A base end portion 205a (a near end) of the hollow pipe line 205 is connected to a side of a head portion 206a (a far end) of a handle-side housing 206 (as a first insertion portion) which is made of a rigid pipe member. In the handle-side housing 206, a communication passage 207 is provided, which is joined to the hollow pipe line 205. In addition, to the head portion 206a of the handle-side housing 206, a magnet 208 is fastened, which has a surface finished so that the surface can easily slide on a body wall W1.

A head portion 205b of the hollow pipe line 205 is connected to a base end portion 209a of a head housing member 209 (as a third insertion portion) made of a rigid pipe member. A head portion 205b of the hollow pipe line 205 is joined to a communication passage 210 of the head housing member 209. To a base end portion 209a of the head housing member 209, a magnet 211 is fastened, which has a surface finished so that the surface can easily slide on the body wall W1.

The hollow pipe line 205 consists of a first offset portion 205c including a part extending in a radial direction with respect to the axis of the handle-side housing 206, a second insertion portion 205d which is bent but generally arranged parallel to the axis of the handle-side housing 206, and a second offset portion 205e connected to the head housing member 209.

According to the above-described structure, a channel 212 (an inner hole) as a continuous inner pipe line is formed through the communication passage 207 of the handle-side housing 206, the hollow pipe line 205, and the communication passage 210 of the head housing member 209. A treatment tool 220 for a soft endoscope is inserted into the channel 212 from the base end side of the handle-side housing 206, where the tool 220 has a length corresponding to the length of the channel 212.

The treatment tool 220 has a handle portion 221 from which an insertion portion 222 extends. A head treatment portion 223 for performing treatment is provided at the head of the insertion portion 222.

The insertion portion 222 has a flexible coil 224 which can transmit torque. A wire 225 passes through the coil 224 in a manner such that the wire 225 can freely move forward or backward. A specific length of a head portion 224a of the coil 224 is not flexible, where this length substantially coincides with the length of the head housing member 209. Similarly, a specific length of a base end portion 224b of the coil 224, closer to the handle portion 221, is not flexible, where this length substantially coincides with the length of the handle-side housing member 206. Therefore, if the head portion 224a or the base end portion 224b of the coil 224 protrudes from the housing member 206 or 209, the protruding portion is not bent.

Figure 17:
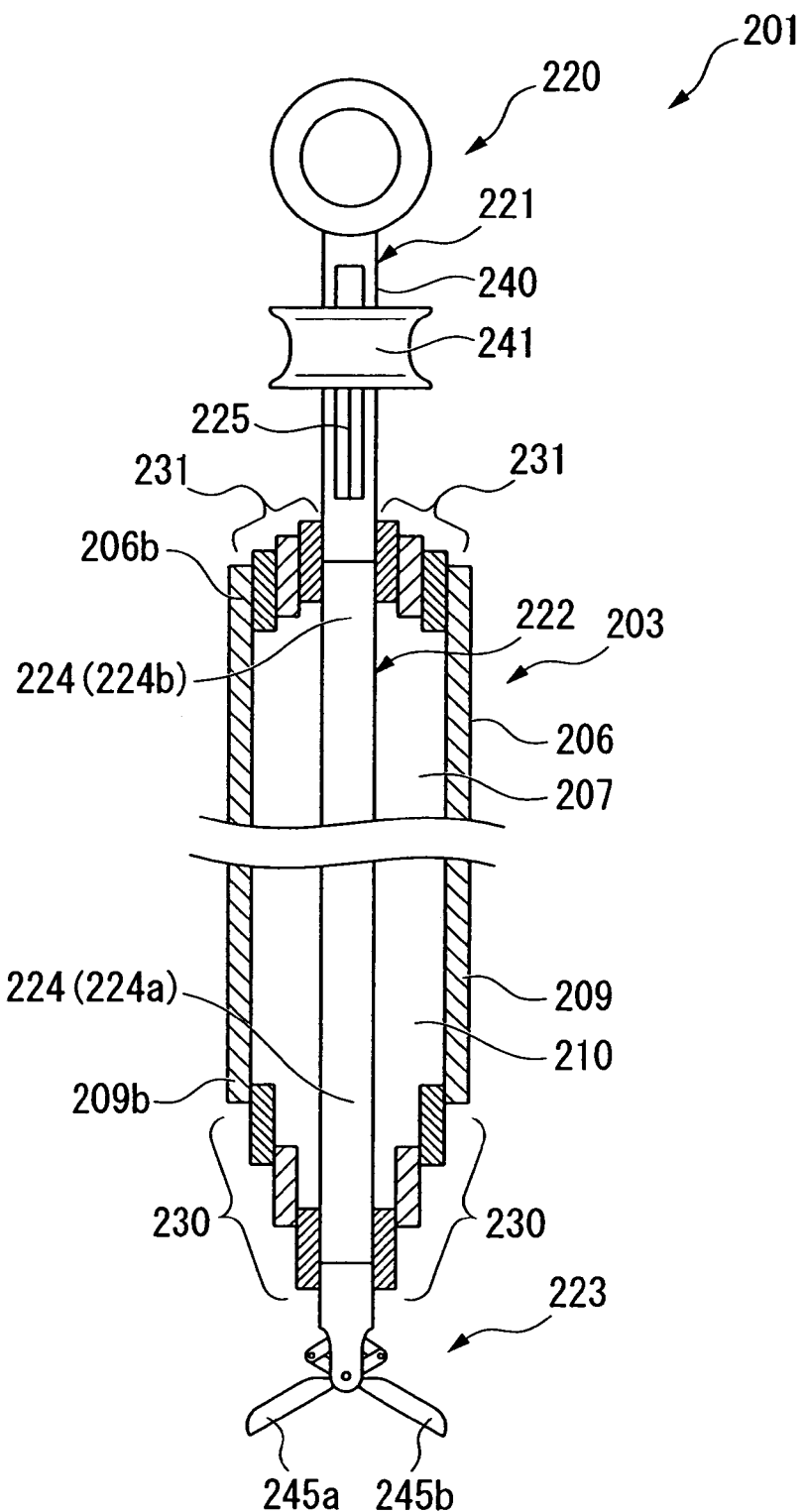
FIG. 17 is a diagram showing an example of the structure of a head portion and a base end portion of an insertion section.

As shown in FIG. 17, when a multiple thrust mechanism 231 is provided at a base end portion 206b of the handle-side housing 206 so as to support the base end portion 224b in the insertion portion 222, the rigidity can be improved. Similarly, when a multiple thrust mechanism 230 is provided at a head portion 209b of the head housing member 209 so as to support the head portion 224a in the insertion portion 222 of the treatment section 220, the rigidity can also be improved.

The handle portion 221 as shown in FIG. 16 has a fixed handle member 240 and a movable handle member 241 which can slide along the fixed handle member 240 (in the longitudinal axial direction). To the fixed handle member 240, the base end portion 224b of the coil 224 is fastened. To the movable handle member 241, a base end portion of the wire 225 is fastened.

The head treatment portion 223 has a pair of clipping members 245a and 245b which can be freely opened and closed. Base ends of the clipping members 245a and 245b are respectively connected to link members 180a and 180b in a freely rotatable form. Ends of the link members 180a and 180b are connected to a head portion of the wire 225 in a freely rotatable form. The pair of clipping members 245a and 245b can be opened or closed by moving the wire 225 forward or backward.

The operation of the present embodiment will be explained below.

After the head housing member 209 is inserted into a coelom through a trocar W2, the magnet 208, provided at the head of the handle-side housing, is made to approach the body wall. Accordingly, the magnet 211, provided at the base end side of the head housing member 209, is pulled toward the body wall by magnetic force. Simultaneously, the hollow pipe line 205 is bent so that the handle-side housing 206 and the head housing member 209 are linearly arranged on either side of the body wall. In this state, when the handle portion 221 is moved along the body wall, the hollow pipe line 205 is bent because magnetic force generated by the magnets 208 and 211 is greater than a force against bending of the hollow pipe line 205. A linear arrangement of the handle-side housing 206 and the head housing member 209 is maintained. When the handle portion 221 is moved along the body wall W1, the head treatment portion 223 moves in the same direction as the direction of the movement of the handle portion 221, similarly to when in a state in which no trocar W2 is present.

When the handle portion 221 is pushed toward the body wall W1 while the position of the handle-side housing 206 is maintained, and the treatment tool 220 proceeds along the channel 212. The head treatment portion 223 then protrudes from the head of the head housing member 209, where the amount of protrusion coincides with the amount of pushing (i.e., the moving distance) of the handle portion 221. In this process, the head portion 224a of the coil 224 is not flexible; thus, when this portion protrudes from the head housing member 209, various operations can be performed without bending. When the handle portion 221 is withdrawn from the body wall, the treatment tool 220 is withdrawn along the channel 212. The head treatment portion 213 is also withdrawn, where the amount of withdrawal coincides with the amount of withdrawal of the handle portion 221. During the above operations, the distance and the positional relationship between the handle portion 221 and the head treatment portion 223 are maintained to be constant. The head treatment portion 223 moves together with the handle portion 221, similarly in a state in which no body wall W1 is present.

When the handle portion 221 is rotated with respect to the handle-side housing 206, the rotation is transmitted via the coil 224 to the head treatment portion 223, and the head treatment portion 223 rotates by the same amount of rotation as that of the rotation of the handle portion 221.

When the movable handle member 241 is moved forward or backward along the fixed handle member 240, the wire 225 also moves forward or backward. Therefore, the clipping members 245a and 245b, coupled to the wire 225 via the link members 180a and 180b, are opened or closed.

According to the present embodiment, through a single trocar W2, a wider area treatment is possible in comparison with conventional instruments. The number of trocars W2 necessary in a surgical operation can be reduced, and a time period necessary for inserting trocars W2 in a body wall W1 and a time period necessary for pulling out the treatment tool from a trocar W2 and inserting the tool through another trocar W2 can be reduced, thereby reducing a time necessary for each surgical operation and also reducing damage to the patient.

In addition, the treatment section and the operation section are substantially coaxially arranged; thus, it is easy for the operator to intuitively know the position of the treatment section, and the operator can easily operate the treatment tool.

In conventional instruments, an operation section must be moved for a trocar as a fulcrum in a direction opposite to a direction in which a treatment section is moved in a coelom. In this case, the operation is not performed intuitively, and thus considerable time is necessary for the operator to become experienced. According to the present embodiment, the direction in which the handle portion 221 of the treatment tool 220 or the handle-side housing 206 moves coincides with that of the head treatment portion 223 or the head housing member 209, in any case of vertical, right-left, or front-back movement. Therefore, an intuitive operation can be performed, and less time is necessary for the operator to become experienced.

Fourth Embodiment

Figure 18:
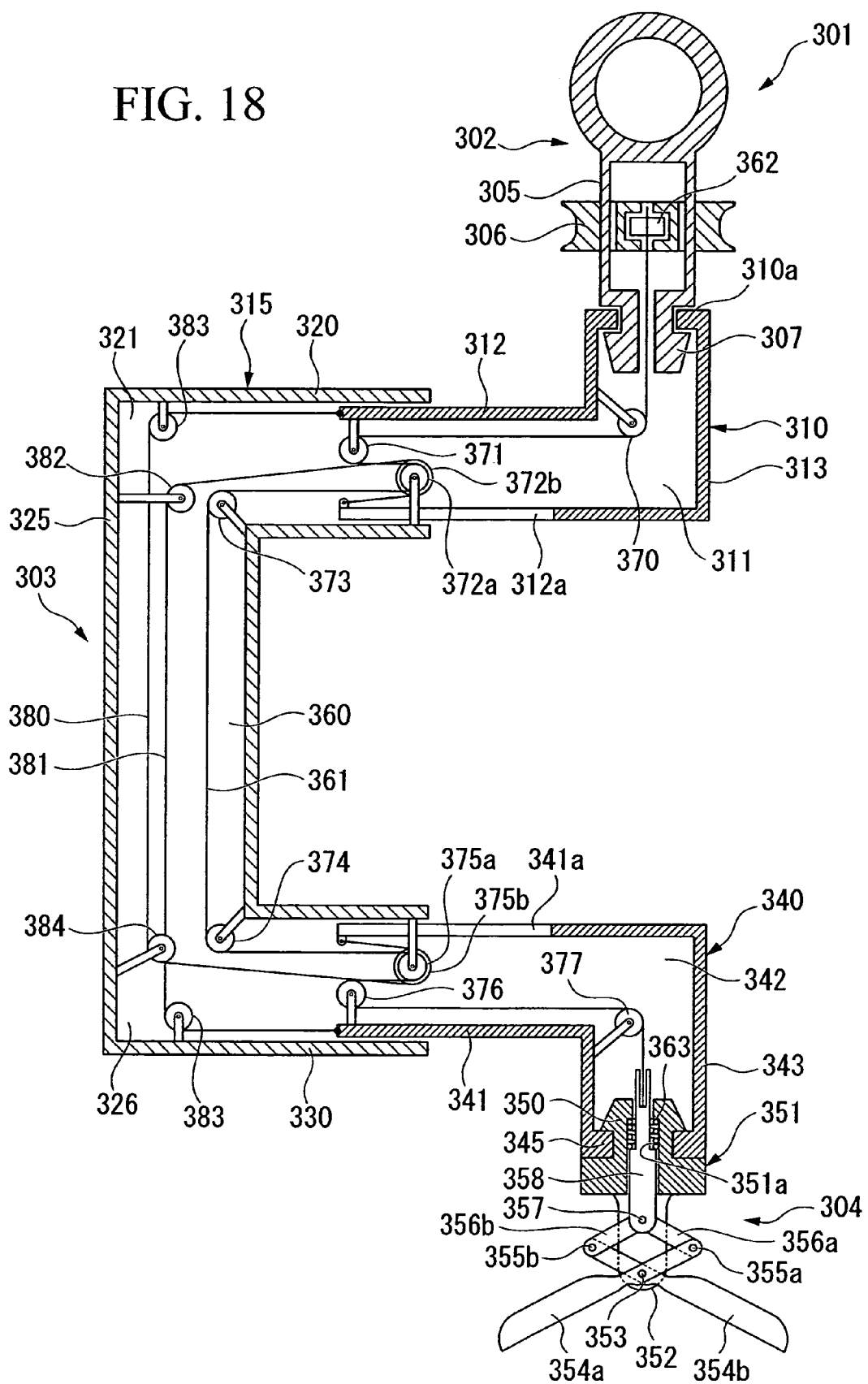
FIG. 18 is a sectional view showing the structure of a surgical treatment tool as the instrument for the endoscope.

FIG. 18 shows a surgical treatment tool as a fourth embodiment of the instrument for the endoscope.

A surgical treatment tool 301 has an insertion section 303 extending from the head of an operation section 302, and a treatment section 304 is provided at the head of the insertion section 303.

The operation section 302 has a fixed handle member 305 and a movable handle member 306 which can freely advance or withdraw along the fixed handle member 305 along the axis thereof. A hook 307 is provided at the head side of the fixed handle member 305. The hook 307 is inserted in a freely rotatable form through a smaller-inner-diameter portion 310a as a base end portion (a near end) of a handle-side connection member 310 which is made of an L-shaped hollow member. Accordingly, the fixed handle member 305 can be rotated with respect to a first insertion portion 313 of the handle-side connection member 310.

The insertion section 303 includes the handle-side connection member 310 which has a first bent portion 311 at a head portion (a far end) of the first insertion portion 313. The first insertion portion 313 is parallel to the axis of the operation section 302. The handle-side connection member 310 bends perpendicularly at the first bent portion 311, and has a slide portion 312 extending from the bent portion 311 in a direction perpendicular to the axis of the operation section 302. A head portion of the slide portion 312 is fit to a base end portion of a guide portion 320 of an intermediate connection member 315 in a manner such that the fit portion can freely advance or withdraw.

The intermediate connection member 315 has a second bent portion 321 at an end portion of the guide portion 320. The second bent portion 321 bends perpendicularly, and a second insertion portion 325 extends from the second bent portion 321 parallel to the axis of the operation section 302. A third bent portion 326 is provided at the head of the second insertion portion 325. The third bent portion 326 bends perpendicularly, and a guide portion 330 extends from the third bent portion 326, where the guide portion 330 is perpendicular to the second insertion portion 325. The guide portion 330 is arranged parallel to the guide portion 320. The intermediate connection member 315 is a hollow member having a general shape close to that of the letter U. To a head portion of the guide portion 330 of the intermediate connection member 315, a base end portion of a slide portion 341 of a head connection member 340 is fit in a manner such that the fit portion can freely advance or withdraw. The head connection member 340 has a fourth bent portion 342 at a head portion of the slide portion 341 which extends parallel to the guide portion 330. The fourth bent portion 342 bends perpendicularly, and a third insertion portion 343 extends from the fourth bent portion 342 parallel to the axis of the operation section 302. Therefore, the head connection member 340 is a hollow member having a general shape close to that of the letter L.

The third bent portion 326 close to the head of the intermediate connection member 315 and the fourth bent portion 342 of the head connection member 340 are made of an elastic material, and thus can have substantially linear forms when being inserted into a trocar W2. However, the third bent portion 326 and the fourth bent portion 342 have a certain degree of hardness by which they are not deformed by external force applied when treatment is performed after the insertion into a living body. In addition, the distance between the second bent portion 321 and the third bent portion 326 of the intermediate connection member 315 is sufficiently longer than the length of the trocar W2 into which the surgical treatment tool 301 is inserted. Therefore, the surgical treatment tool 301 can be advanced or withdrawn for the trocar W2 while the section from the second bent portion 321 to the third bent portion 326 of the intermediate connection member 315 is inserted into the trocar W2.

In the insertion portion 303, the slide portion 312 of the handle-side connection member 310 and the guide portion 320 of the intermediate connection member 315 form a first offset portion which can freely expand or contract. The guide portion 330 of the intermediate connection member 315 and the slide portion 341 of the head connection member 340 form a second offset portion which can freely expand or contract. The direction of the expansion and contraction is perpendicular to the axis of the operation section 302 and the treatment section 304.

In the head connection member 340, a hook 350 of the treatment section 304 is fit through a smaller-inner-diameter portion 345 of the third insertion portion 343. The hook 350 is provided at a base end side of a head connection member 351. The hook 350 restricts movement of the head housing member 351 with respect to the head connection member 340 in the axial direction. However, the head connection member 351 is freely rotatably connected to the head connection member 340 around the axis thereof. The head connection member 351 has a through hole 351a in the axial direction.

From a head portion of the head housing member 351, a pair of supports 352 extends, and a center part of a pair of clipping members 354a and 354b is supported in a freely rotatable form by a pin 353 which is mounted to the supports 352. At the base end sides of the pair of clipping members 354a and 354b, ends of link members 356a and 356b are respectively supported by pins 355a and 355b in a freely rotatable form. The other ends of the link members 356a and 356b are fastened to a head portion of a wire connection member 358 via a pin 357.

In the insertion section 303, inner pipe lines of the handle-side connection member 310, the intermediate connection member 315, and the head connection member 340 are joined and communicate with each other, thereby forming a working channel 360 (i.e., an inner hole). A wire 361 (i.e., a driving force transmitting device) passes through the channel 360. The wire 361 is a metal wire having a superior torque transmitting performance. A base end portion of the wire 361 is drawn into the operation section 302 and fastened to a wire holding member 362 by a method such as brazing or clamping. The wire holding member 362 is fastened to the movable handle member 306 by a method such as press fitting or adhesion. A head portion of the wire 361 is fastened to the base end side of the wire connection member 358 by a method such as brazing, clamping, or adhesion. The wire connection member 358 is forced toward the head side by an elastic member such as a coil spring 363. Therefore, when the operation section 302 is operated, the operation is transmitted via the wire 361 to the treatment section 304, so that the pair of clipping members 354a and 354b is opened, closed, or rotated.

In the channel 360, a pulley 370 is attached to the first bent portion 311 of the handle-side connection member 310. To a head portion of the slide portion 312 of the handle-side connection member 310, a pulley 371 is attached. To a base end portion of the guide portion 320 of the intermediate connection member 315, pulleys 372a and 372b are attached, each of which can independently rotate. A pulley 373 is attached to the second bent portion 321 of the intermediate connection member 315. A pulley 374 is attached to the third bent portion 326 of the intermediate connection member 315. Additionally, pulleys 375a and 375b are attached to a head portion of the intermediate connection member 315. Each of the pulleys 375a and 375b can independently rotate. A pulley 376 is attached to a base end portion of the slide portion 341 of the head connection member 340. A pulley 377 is attached to the fourth bent portion 342 of the head connection member 340. The wire 361 is hung on each of the pulleys 370, 371, 372a, 373, 374, 375a, 376, and 377 in turn.

The handle-side connection member 310 and the head connection member 340 are connected via wires 380 and 381 passing through the channel 360. The wires 380 and 381 (driving force transmitting devices) are made of a metal material having low expandability, and may be made of a super fiber such as Kevlar.

A base end portion of the wire 380 is fastened to a head portion of the slide portion 312 of the handle-side connection member 310. In the channel 360, the wire 380 is hung on a pulley 383 attached to the second bent portion 321 of the intermediate connection member 315, a pulley 384 attached to the third bent portion 326, and a pulley 375b attached to a head portion of the guide portion 330 of the intermediate connection member 315 in turn, and then fastened to the base end of the slide portion 341 of the head connection member 340.

A base end portion of the wire 381 is fastened to a head portion of the slide portion 312 of the handle-side connection member 310. In the channel 360, the wire 381 is hung on a pulley 372b attached to a base end portion of the guide portion 320 of the intermediate connection member 315, a pulley 382 attached to the second bent portion 321, and a pulley 383 attached to the third bent portion 326 in turn, and then fastened to a base end portion of the slide portion 341 of the head connection member 340.

The lengths of the wires 380 and 381 are adjusted so that the operation section 302 and the treatment section 304 are coaxially arranged. In the slide portion 312 of the handle-side connection member 310, a slit 312a is provided so as to accept the pulleys 372a and 372b of the intermediate connection member 315. Similarly, in a base portion of the head connection member 340, a slit 341a is provided so as to accept the pulleys 375a and 375b of the intermediate connection member 315. According to the slits 312a and 341a, the handle-side connection member 310 and the head connection member 340 can move for the intermediate connection member 315 without interfering with the pulleys 372a, 372b, 375a, and 375b.

The operation of the present embodiment will be explained below.

When the third insertion portion 343 is inserted into a coelom, the third bent portion 326 of the intermediate connection member 315 and the fourth bent portion 342 of the head connection member 340, made of an elastic material, can be transformed into a substantially linear form.

When the fixed handle member 305 of the operation section 302 is rotated with respect to the handle-side connection member 310 of the insertion section 303, the wire 361 rotates. The rotation is transmitted to the head housing member 351 via the wire 361, and the treatment section 304 rotates with respect to the head connection member 340.

When the movable handle member 306 is withdrawn along the fixed handle member 305, the wire 361 pulls the wire connection member 358 toward the base end side against a force by the spring 363, so that the pair of clipping members 354a and 354b are closed. When the movable handle member 306 is released, the pair of clipping members 354a and 354b are opened by the force of the spring 363.

When the operation section 302 is moved parallel to a body wall W1 (e.g., in a horizontal direction) so that the operation section 302 approaches the intermediate connection member 315, the base end portion of the wire 381 is pulled, and the head connection member 340, to which the head portion of the wire 381 is fastened, is drawn toward the intermediate connection member 315. In this process, the treatment section 304 moves in the same direction as the direction in which the operation section 302 moves. When the operation section 302 is moved parallel to the body wall W1 (e.g., in a horizontal direction) so that the operation section 302 leaves the intermediate connection member 315, the base end portion of the wire 380 is pulled, and the head connection member 340, to which the head portion of the wire 380 is fastened, is drawn so that the head connection member 340 leaves the intermediate connection member 315. In this process, the treatment section 304 moves in the same direction as the direction in which the operation section 302 moves.

According to the present embodiment, through a single trocar W2, a wider area treatment is possible in comparison with conventional instruments. The number of trocars W2 necessary in a surgical operation can be reduced, and a time period necessary for inserting trocars W2 in a body wall W1 and a time period necessary for pulling out the treatment tool from a trocar W2 and inserting the tool through another trocar W2 can be reduced, thereby reducing a time necessary for each surgical operation and also reducing damage to the patient.

In addition, the treatment section 304 and the operation section 302 are substantially coaxially arranged; thus, it is easy for the operator to intuitively know the position of the treatment section 304, and the operator can easily operate the treatment tool.

In conventional instruments, an operation section must be moved around a trocar as a fulcrum in a direction opposite to a direction in which a treatment section is moved in a coelom. In this case, the operation is not performed intuitively, and thus considerable time is necessary for the operator to become experienced. According to the present embodiment, the direction in which the operation section 302 moves coincides with that of the treatment section 304, in any case of vertical, right-left, or front-back movement. Therefore, an intuitive operation can be performed, and less time is necessary for the operator to become experienced.

In addition, in conventional instruments which receive more restriction from the trocar, approach to a specific position in a coelom is permitted only in a single direction depending on the position where the trocar is mounted. Therefore, it is difficult for the operator to perform the operation. In the present embodiment, the direction of approach to a specific position in a coelom can be changed by adjusting the offset amount of the treatment section 304 for the trocar W2 (in the direction perpendicular to the axis of the trocar W2), or the amount of insertion along the axis of the trocar W2. Therefore, the operation can be performed considerably easily. It is unnecessary to consciously perform the above adjustment of the offset amount or the amount of insertion. Such adjustment is possible when the operator moves the operation section 302 with a feeling as if the trocar W2 were not present. As the operation can be easily performed, treatment can be performed more safely and reliably. Therefore, a time period necessary for each surgical operation can be reduced, and both patient and operator receive less burden.

Figure 19:
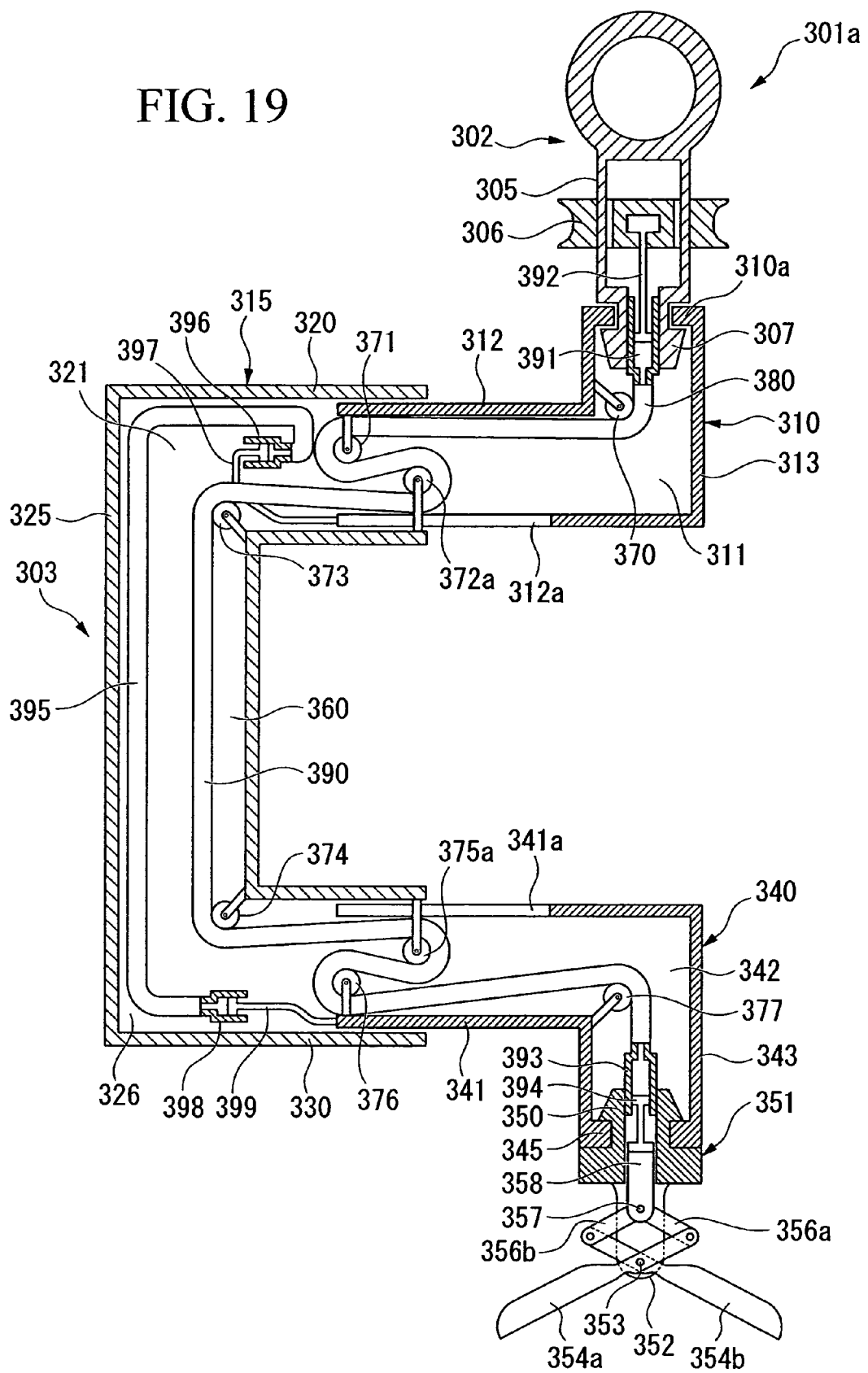
FIG. 19 is a sectional view showing a structure in which a tube is used instead of a wire.

Instead of the wire 361, A tube containing a fluid may be used for transmitting the opening/closing operation or the rotation to the treatment section 304. FIG. 19 shows a surgical treatment tool 301a as an example. A tube 390 (i.e., a driving force transmitting device) is coupled to the operation section 302, and is hung on the pulleys 371, 372a, 373, 374, 375a, 376, and 377 in turn, and is coupled to the head housing member 351 of the operation section 302. The base end side of the tube 390 is connected to a cylinder 391 which is fixed in the fixed handle member 306. In the cylinder 391, a piston 392, which is fastened to the movable handle member 306, is slidably arranged. The head side of the tube 390 is connected a cylinder 393 which is fixed in the head housing member 351. In the cylinder 393, a piston 394, which is connected to the base end side of the wire connection member 358, is slidably inserted. The tube 390 is made of a flexible material, and is filled with a fluid such as physiological saline (solution), oil, or air.

Instead of the wires 380 and 381, a tube 395 (i.e., a driving force transmitting device) is used. The tube 395 is fixed along the intermediate connection member 315 and is connected to a cylinder 396 in the guide portion 320 of the intermediate connection member 315. In the cylinder 396, a piston 397 is inserted from the side where the second bent portion 321 is present, parallel to the axis of the guide portion 320 of the intermediate connection member 315, in a manner such that the piston 397 can freely slide. The piston 397 is fastened to the head portion of the handle-side connection member 310. To a head portion of the tube 395, a cylinder 398 is connected. In the cylinder 398, a piston 399 is inserted from the side where the head connection member 340 is present, parallel to the axis of the guide portion 330 of the intermediate connection member 315, in a manner such that the piston 397 can freely slide. The piston 399 is connected to the slide portion 341 of the head connection member 340. The tube 395 is filled with a fluid such as physiological saline, oil, or air.

In the surgical treatment tool 301a, the opening/closing operation is transmitted from the operation section 302 to the treatment section 304 via a fluid such as physiological saline. Power is transmitted via a fluid such as physiological saline, provided in the tube 395, and the cylinders 396 and 397; thus, the treatment section 304 moves in the same direction as the direction in which the operation section 302 moves. According to the surgical treatment tool 301a, a more exact feel for grasping a tissue, or a more subtle force applied to the heads of the clipping members 132a and 132b is transmitted to the operator, thereby allowing safer treatment. The other effects obtained by the surgical treatment tool 301a are the same as those obtained by the surgical treatment tool 301.

Figure 20:
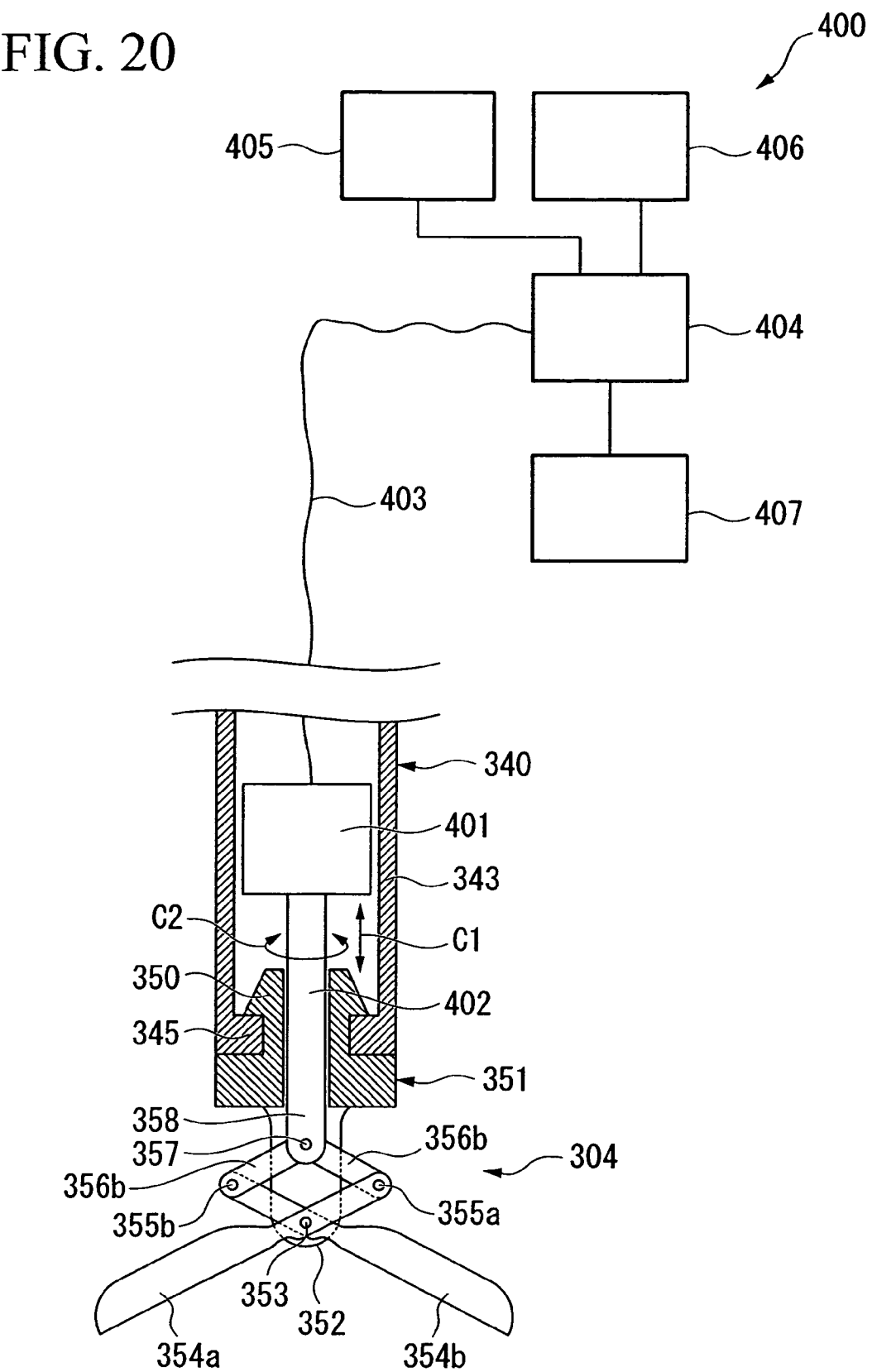
FIG. 20 is a sectional view showing a part of a structure in which an ultrasonic motor is used instead of a wire.

As shown in FIG. 20, instead of the wire 361, an ultrasonic motor 401 connected to the head connection member 340 may be used. An output shaft 402 of the ultrasonic motor 401 can be driven in either of (i) a direct acting direction (indicated by the arrow C1 in FIG. 20) for moving forward or backward along the axis of the head connection member 340, and (ii) a rotational direction (indicated by the arrow C2 in FIG. 20) around the axis of the head connection member 340. To a head portion of the output shaft 402 of the ultrasonic motor 401, the base end portions of the link members 356a and 356b are coupled via a pin 357 in a freely rotatable form.

To the ultrasonic motor 401, a signal output from a motor driver 404 is sent via a signal line 403. The motor driver 404 is connected to a position sensor 405, an encoder 406, and a power supply 407. The position sensor 405 is provided in the operation section 302, so as to measure the position of the movable handle member 306 with respect to the fixed handle member 305 in the operation section 302. The encoder 406 measures an amount of rotation when the operation section 302 is rotated with respect to the handle-side connection member 310. Based on data output from the position sensor 405 and the encoder 406, the motor driver 404 controls the ultrasonic motor 401 so that a degree of opening/closing and an amount of rotation of the pair of the clipping members 354a and 354b of the treatment section 304 coincide with an amount of movement of the operation section 302 (corresponding to an amount of movement of the movable handle member 306) and an amount of rotation of the operation section 302. Instead of the motor driver 404, another kind of an actuator such as a DC (direct current) motor may be used.

In treatment, the operation section 302 is rotated with respect to the handle-side connection member 310. The encoder 406 measures the amount of rotation. The motor driver 404 sends and outputs a signal to the ultrasonic motor 401 so that the output shaft 402 rotates in the direction C2 in accordance with the measured amount of rotation. Accordingly, the treatment section 304 rotates with respect to the head connection member 340.

When the movable handle member 306 is withdrawn along the fixed handle member 305, the position sensor 405 measures the amount of this movement. The motor driver 404 sends an output signal to the ultrasonic motor 401 so that the output shaft 402 withdraws in the direction C1 in accordance with the measured amount of movement. Accordingly, the pair of clipping members 354a and 354b is closed. When the movable handle member 306 is advanced along the fixed handle member 305, the position sensor 405 measures the amount of this movement, similarly. The motor driver 404 outputs and sends a signal to the ultrasonic motor 401 so that the output shaft 402 advances in the direction C1 in accordance with the measured amount of movement. Accordingly, the pair of clipping members 354a and 354b is opened. Effects obtained by the surgical treatment tool 400 are similar to those obtained by the surgical treatment tool 301.

Figure 21:
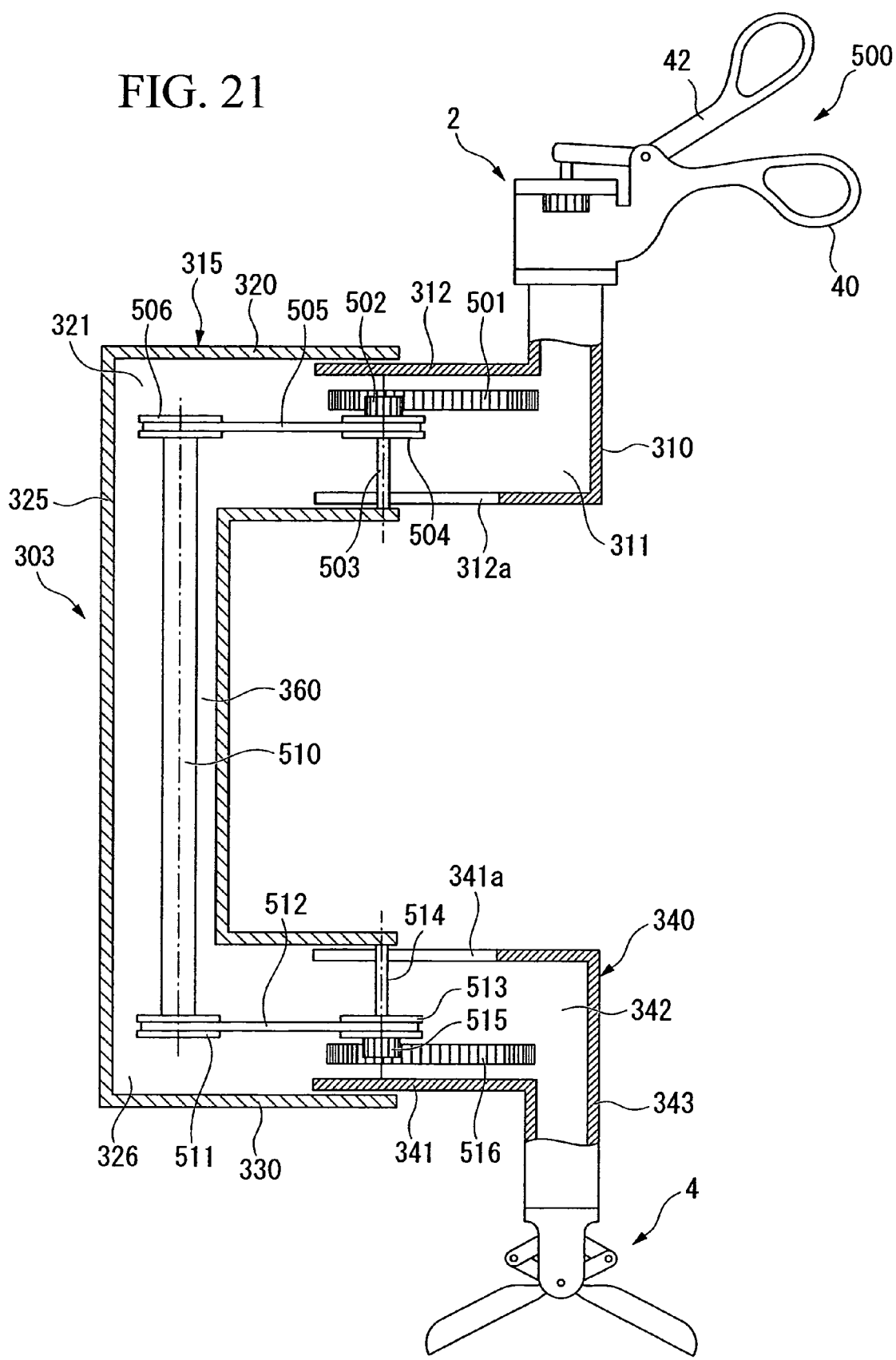
FIG. 21 is a sectional view showing a part of a structure in which a rack and pinion mechanism and a pulley mechanism are used instead of a wire.

As shown in FIG. 21, a rack and pinion mechanism and a pulley mechanism may be used. In a surgical treatment tool 500, a rack 501 is fastened to the head portion of the handle-side connection member 310. The rack 501 is engaged with a pinion 502 which is attached to the base end portion of the intermediate connection member 315 in a freely rotatable form. A shaft 503 extends in a direction perpendicular to the axis of the slide portion 312. The pinion 502 is fastened to a pulley 504 which is fastened to the shaft 503 where the pinion 502 and the pulley 504 are integrally formed. A belt 505 is hung around (an outer periphery of) the pulley 504. This belt 505 is also hung around (an outer periphery of) a pulley 506 which is arranged in the second bent portion 321. The shaft 510 functions as the rotation shaft of the pulley 506, and is attached to the intermediate connection member 315, parallel to the axis of the second insertion portion 325 in a freely rotatable form. A head portion of the shaft 510 reaches the third bent portion 326 in which a pulley 511 is attached to the shaft. A belt 512 is hung around (an outer periphery of) the pulley 511. The belt 512 is also hung around (an outer periphery of) a pulley 513 which is contained in the head connection member 340 and is attached to a shaft 514 and a pinion 515. The shaft 514 is attached to the head portion of the guide portion 330 of the intermediate connection member 315 in a freely rotatable form. The pinion 515 is engaged with a rack 516 which is fastened to a base end portion of the slide portion 341 of the head connection member 340, parallel to the axis of the slide portion 341. In FIG. 20, the coil 31 or the wire 32 for transmitting a driving force from the operation section 302 is not shown.

In treatment, the operation section 302 is made to approach the intermediate connection member 315. The pinion 502 then rotates around the shaft 503, and accordingly, the pulley 504 rotates. This rotation is transmitted via the belt 505 to the pulley 506, and the pulley 511 also rotates in the same direction via the shaft 510. The rotation of the pulley 511 is transmitted via the belt 512 to the pulley 513. The pinion 515 fastened to the pulley 513 then rotates around the shaft 514. The rack 516, engaged with the pinion 515, is fastened to the head connection member 340; thus, the head connection member 340 and the treatment section 304 move toward the intermediate connection member 315, as the operation section 302 moves. When the operation section 302 is moved so that the operation section 302 leaves the intermediate connection member 315, rotation is also transmitted similarly, and the treatment section 304 also moves so as to leave the intermediate connection member 315. When the rack and pinion mechanism close to the operation section 302 and the rack and pinion mechanism close to the treatment section 304 have the same structure, the amount and the direction of movement of the operation section 302 coincide with those of the treatment section 304. Effects obtained by the surgical treatment tool 500 are similar to those obtained by the surgical treatment tool 301.

The embodiments are not limited to the above-descried structures, and any appropriate combination between embodiments may be possible.

Figure 22:
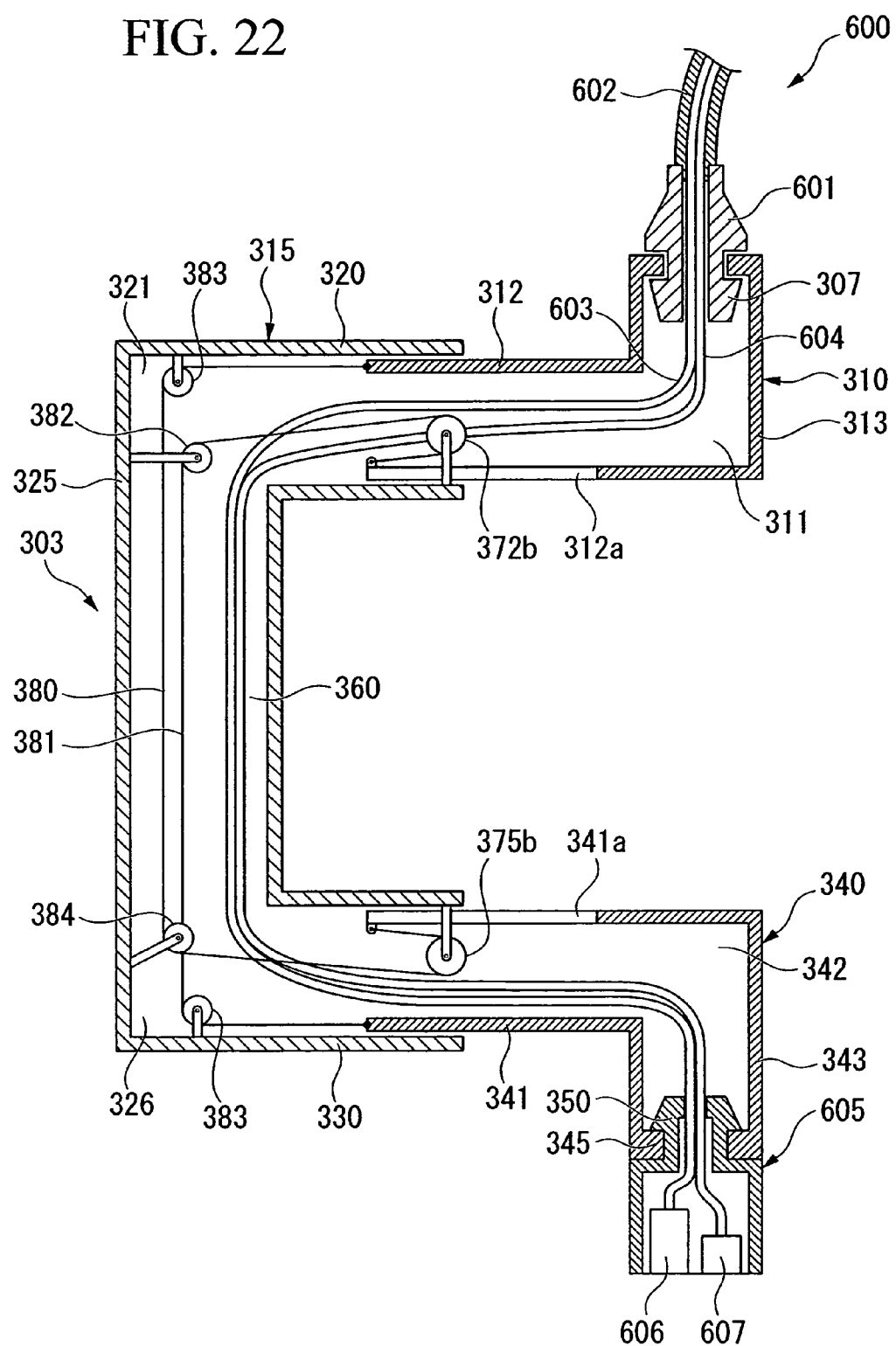
FIG. 22 is a diagram showing the structure of an observation instrument as the instrument for the endoscope.
Figure 23:
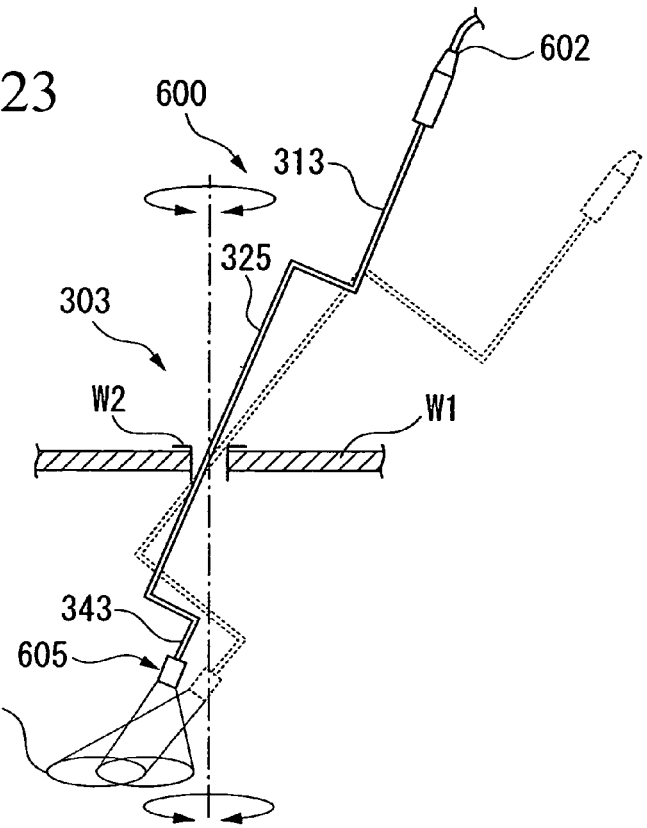
FIG. 23 is a diagram showing a method of using the observation instrument.
Figure 24:
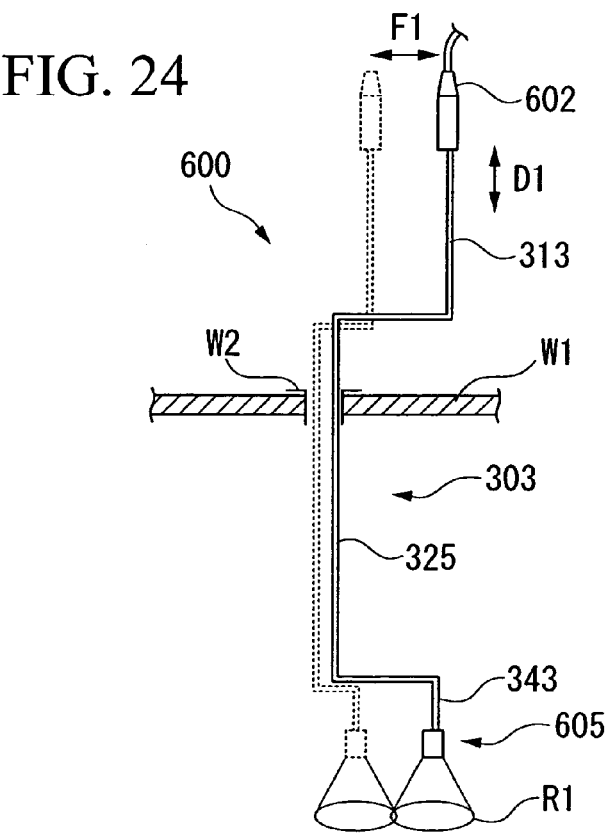
FIG. 24 is a diagram showing a method of using the observation instrument.

In the above embodiments, the instrument for the endoscope may be an observation instrument having an imaging device such as a CCD (charge coupled device) or a CMOS (complementary metal oxide semiconductor) instead of the treatment section 4, 104, or 304, or the head treatment section 223. The part to be observed can be changed by a function similar to that described in either embodiment. In comparison with a conventional hard endoscope, a wider area observation is possible. The position of the operation section 2, 102, 302, or the handle 221 and the position of an observation device provided at the head of the instrument have a constant relationship. Therefore, it is possible to solve a problem of a conventional endoscope having a bent structure in which it is difficult to understand the observation direction, and possible to intuitively change the observed part. FIG. 22 shows an example of an observation instrument. An observation instrument 600 has an insertion section 303. To a smaller-inner-diameter portion 310a of a handle-side connection member 310, an adaptor 601 is attached, to which a cord 602 is joined. The cord 602 includes a video cable 603 and an electric cable 604 which are coated. The video cable 603 and the electric cable 604 pass through the insertion section 303 and reach an observation section 605 provided on the head side. The observation section 605 has an imaging unit 606 and a radiating device 607. The imaging unit 606 has an imaging device and an objective optical system, and an image signal output from the imaging device is output to the video cable 603. As the imaging device, a CCD or a CMOS may be used. The radiating device 607 emits light by receiving electric power from the electric cable 604, and may be an LED (light emitting diode). The position of the second insertion portion 325 is offset with respect to the first insertion portion 313 and the third insertion portion 343. Therefore, as shown in FIG. 23, when the first insertion portion 313 side is rotated with respect to the axis of the trocar W2, the position of the observation section 605 can be changed in a coelom, thereby easily changing an observation field R1 of view. As shown in FIG. 24, when the first insertion portion 313 is moved in parallel in a direction F1 with respect to the second insertion portion 325, the third insertion portion 343 moves in the same direction via the wires 380 and 381 (see FIG. 22). The field R1 of view of the third insertion portion 343 is then horizontally moved.

Fifth Embodiment

Figure 25:
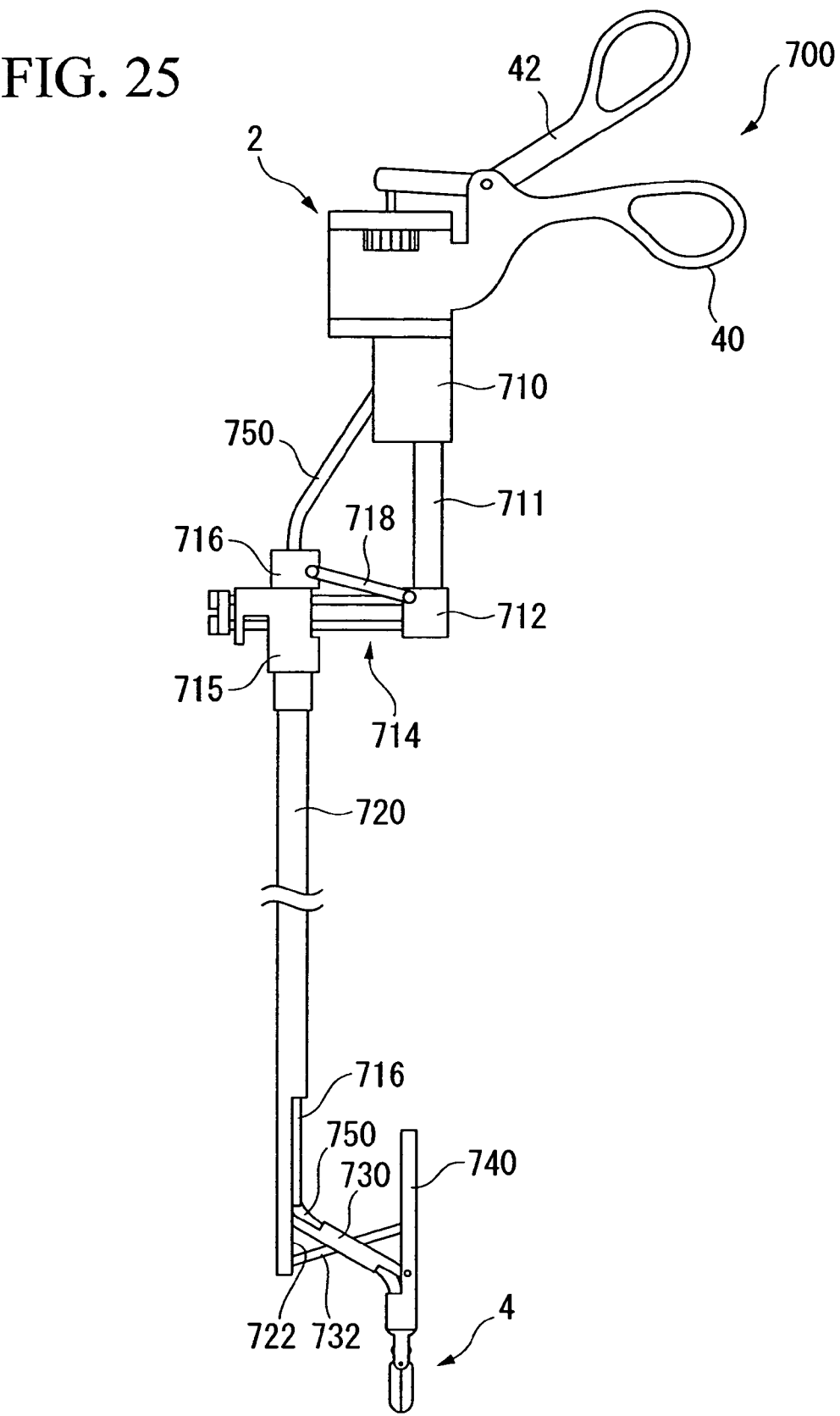
FIG. 25 is a diagram showing the structure of a surgical treatment tool as a fifth embodiment in accordance with the present invention.

FIG. 25 shows a surgical treatment tool 700 as a fifth embodiment of the instrument for the endoscope.

In the surgical treatment tool 700, a member 710 is fastened to the head of the operation section 2, and an operation-section support member 711 is fastened to the head of the member 710. To the head of the operation-section support member 711, a connection member 712 is attached, from which a guide rail 714 extends in a direction substantially perpendicular to the axis of the operation-section support member 711. A slider 715 is provided, which can slide on the guide rail 714.

The surgical treatment tool 700 has a substantially pipe-shaped insertion portion 720. A tube 750 or the like can pass from the operation section 2 to the treatment section 4 through the insertion portion 720, thereby easily implementing a structure for making the treatment section 4 cooperate with the operation of the operation section 2.

The insertion portion 720 is connected to the slider 715, and a movable rod member 716 (or a rod member) is inserted into the insertion portion 720. The movable rod member 716 is movable along the axis of the insertion portion 720 with respect to the slider 715 and the insertion portion 720 (i.e., is freely movable with respect to the insertion portion 720 along the axis of the insertion portion 720). The movable rod member 716 and the connection member 712 are coupled to each other via a rotatable bar 718. One end of the rotatable bar 718 is supported by the connection member 712 in a freely rotatable form, and the other end of the rotatable bar 718 is supported by the movable rod member 716. This rotatable bar 718 moves the movable rod member 716 along the axis of the insertion portion 720 in cooperation with the movement of the insertion portion 720 so as to approach or be away from the operation-section support member 711 by using the guide rail 714 and the slider 715.

In a head portion (i.e., close to the treatment section 4) of the insertion portion 720, a part of the face which faces the axis of the operation-section support member 711 is removed, thereby producing a recess portion 722. The head portion of the insertion portion 720 is coupled via a link member 730 with a fittable member 740 which is fittable to the recess portion 722. At the head of the fittable member 740, the treatment section 4 is provided.

Conveniently, a portion for connecting the operation section and the treatment section with each other is called the insertion portion. In the present embodiment, the operation-section support member 711, the insertion portion 720, and the fittable member 740 respectively correspond to the first, second, and third insertion portions of the present invention.

The link member 730 has a pipe shape through which the tube 750 passes. The two ends of the link member 730 are respectively coupled to the head of the movable rod member 716 (passing through the insertion portion 720) and the fittable member 740 in a rotatable form. A movable bar 732 is provided in a manner such that the bar 732 and the link member 730 intersect each other. An end of the movable bar 732 is rotatably coupled with the head of the insertion portion 720, and the other end thereof is slidable from the position shown in FIG. 25 along the axis of the fittable member 740 in a direction away from the treatment section 4, and is also rotatably coupled with the fittable member 740. That is, the other end of the movable bar 732 is supported in a freely rotatable form along the axis of the fittable member 740 (that is, along an axial line drawn between the head and the base end of the surgical treatment tool).

Figure 27:
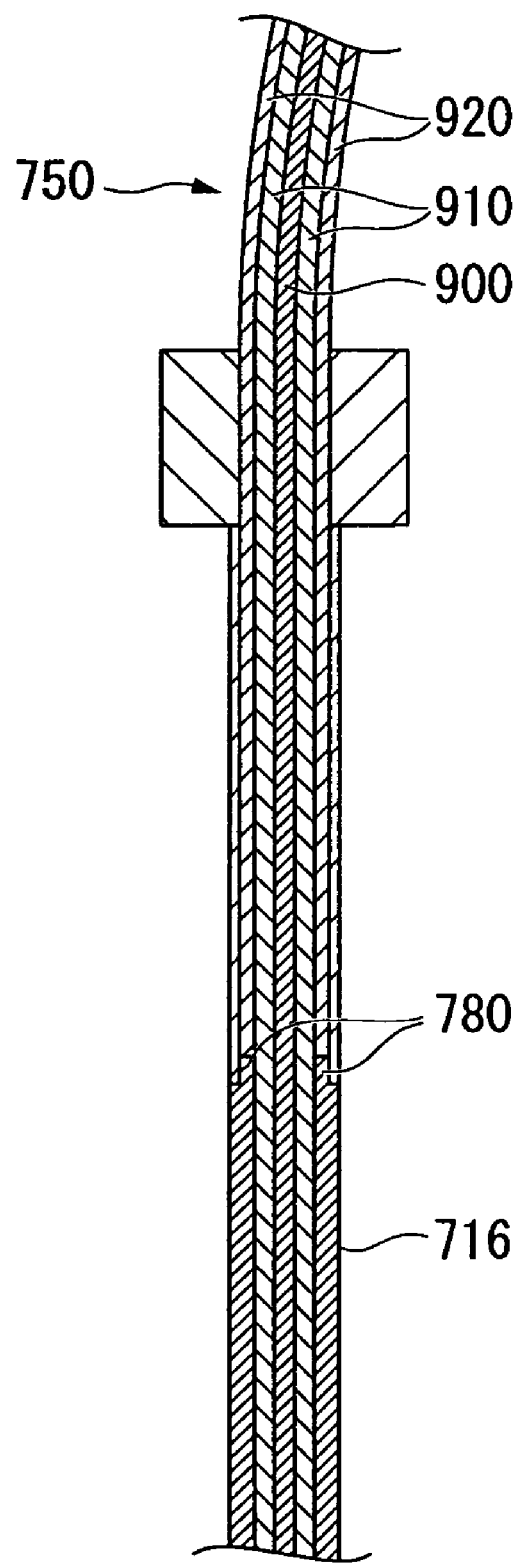
FIG. 27 is a diagram showing the internal structure of a tube and a connection between the tube and a movable rod member in the fifth embodiment.

FIG. 27 is a diagram showing the internal structure of the tube 750 and a connection between the tube 750 and the movable rod member 716. In the tube 750, a wire 900 passes through a treatment section rotating member 910 which has a pipe shape, and the treatment section rotating member 910 is covered with an outer skin portion 920. The outer skin portion 920 may be formed using a coil sheath and a heat-shrinkable tubing provided outside the coil sheath. Two ends of the treatment section rotating member 910 are respectively connected to the treatment section 4 and the operation section 2, and is arranged in a freely rotatable form with respect to the outer skin portion 920. The operation section 2 is supported in a freely rotatable form around the axis of the operation-section support member 711 (i.e., along an axial line drawn between the head and the base end of the operation-section support member), and the treatment section 4 is supported in a freely rotatable form around the axis of the fittable member 740. The rotating motion of the operation section 2 is transmitted via the treatment section rotating member 910 to the treatment section 4, so that the treatment section 4 rotates in accordance with the rotating motion of the operation section 2. The wire 900 passes through the treatment section rotating member 910, and the two ends of the wire 900 are respectively connected to the treatment section 4 and the operation section 2, so that the operation of the operation section 2 is transmitted to the treatment section 4. In the present embodiment, forceps are used as the treatment section 4; thus, the forceps can be opened and closed by operating the operation section 2.

The outer skin portion 920 extends to an outer skin fixing portion 780 provided in the middle of the movable rod member 716. That is, the lower portion (in FIG. 27) of the tube 750 with respect to this fixed position is joined to the movable rod member 716, and cooperates with the axial operation of the movable rod member 716. In contrast, the upper portion of the tube 750 with respect to this fixed position is not fixed to the movable rod member 716; thus, when the movable rod member 716 protrudes so as to be closer to the operation section 2 (see FIG. 26), the upper portion of the tube 750 bends. In this operation, the movable rod member 716 ascends inside the insertion portion 720. Accordingly, the link member 730 coupled to the movable rod member 716 is pulled, and the link member 730 rotates in a direction in which the axis of the link member 730 approaches the axis of the insertion portion 720. In contrast, when the movable rod member 716 descends, the tube 750 is drawn out, and the link member 730 coupled to the movable rod member 716 rotates in the opposite direction.

The link member 730 and the movable bar 732 are coupled with each other at the center position of each member, in a relatively rotatable form. In this case, the link member 730 and the movable bar 732 are supported at the coupling position, thereby improving rigidity. Therefore, it is possible to improve reliability with respect to keeping of a specific position on the side close to the treatment section 4.

That is, when the movable bar 732 slides, the angle between the movable bar 732 and the axis of the insertion portion 720 changes. In this process, the link member 730 symmetrically cooperates with the operation of the movable bar 732, so that the angle between the link member 730 and the axis of the insertion portion 720 also changes.

Figure 26:
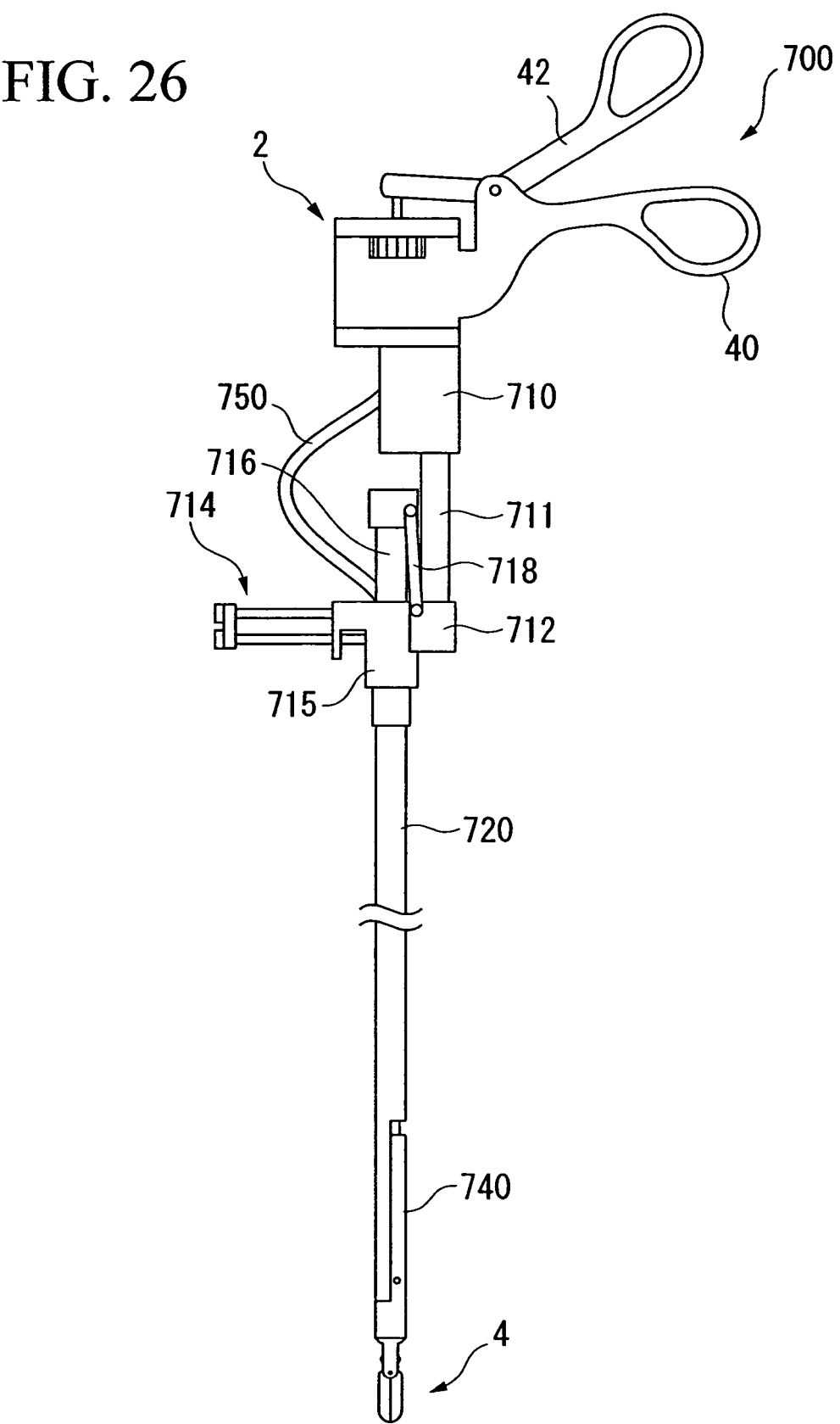
FIG. 26 is a diagram showing another state of the surgical treatment tool shown in FIG. 25.

As shown in FIG. 26, when the surgical treatment tool 700 is inserted into a trocar, the surgical treatment tool 700 can have a substantially linear form (that is, the amount of offset measured when the axes of the fittable member 740 and the insertion portion 720 are substantially linearly arranged is zero).

That is, in the present embodiment, the guide rail 14 functions as a first offset portion (or the first movable joint portion), and the link member 730 and the movable bar 732 function as a second offset portion (or the second movable joint portion). Here, the amount of offset may be approximately 25 mm.

The states shown in FIGS. 25 and 26 can be easily switched between by moving the slider 715 along the path of the first offset portion (i.e., a path along which the operation-section support member 711 and the insertion portion 720 can be away from each other). Specifically, when switching from the state of FIG. 25 to the state of FIG. 26, the slider 715 moves on the guide rail 714 toward the connection member 712, so that the movable rod member 716 moves via the movable bar 718 so to approach the operation section 2. On the treatment section 4 side, in accordance with the upward sliding motion of the base end of the link member 730 together with the movable rod member 716, the movable head of the movable bar 732 coupled with the link member 730 slides upward along the axis of the fittable member 740. In accordance with this sliding operation, the axes of the movable bar 732 and the link member 730 gradually approach the axis of the insertion portion 720. When the axes of the movable bar 732 and the link member 730 are closest to the axis of the insertion portion 720, the surgical treatment tool 700 is in the state shown in FIG. 26, in which the fittable member 740 is substantially contained in the recess portion 722. Additionally, in comparison with the form of the tube 750 in the offset state in FIG. 25, the tube 750 is bent.

As described above, in accordance with the sliding mechanism close to the operation section 2 and the movable link mechanism close to the treatment section 4, the surgical treatment tool 700 can be easily inserted into a trocar, and a head portion (i.e., the treatment section 4) of the surgical treatment tool 700 can be arranged or positioned in a wider area in comparison with conventional tools.

In addition, on the side close to the treatment section 4, the link member 730 and the movable bar 732 form an X shape, thereby producing a truss shape, which improves the rigidity of this portion.

In the present embodiment, the slider 715 is provided at the insertion portion 720, and the guide rail 714 is attached to the operation-section support member 711 by which the operation section 2 is supported. However, embodiments of the present invention are not limited to such a structure, for example, an opposite form may be employed, in which a slider may be provided at an operation-section support member, and a guide rail may be provided at the insertion portion 720. In addition, the arrangement of the link member 730 and the movable bar 732 as shown in FIG. 25 may also be changed to an inverted form. For example, an end of the link member 730 may be connected to the movable rod member 716 at a position closer to the head of the insertion portion 720 in comparison with the position of the movable bar 732, and the other end of the link member 730 may be supported in a freely rotatable form by the fittable member 740 at a position closer to the base end of the fittable member 740 in comparison with the position of the movable bar 732. In this case, one end of the movable bar 732 may be supported in a freely rotatable form by the insertion portion 720, and the other end of the movable bar 732 may be supported by the fittable member 740 in a freely slidable form. Furthermore, in this case, an inner hole may be formed in the movable bar 732 through which the tube 750 passes.

Figure 28:
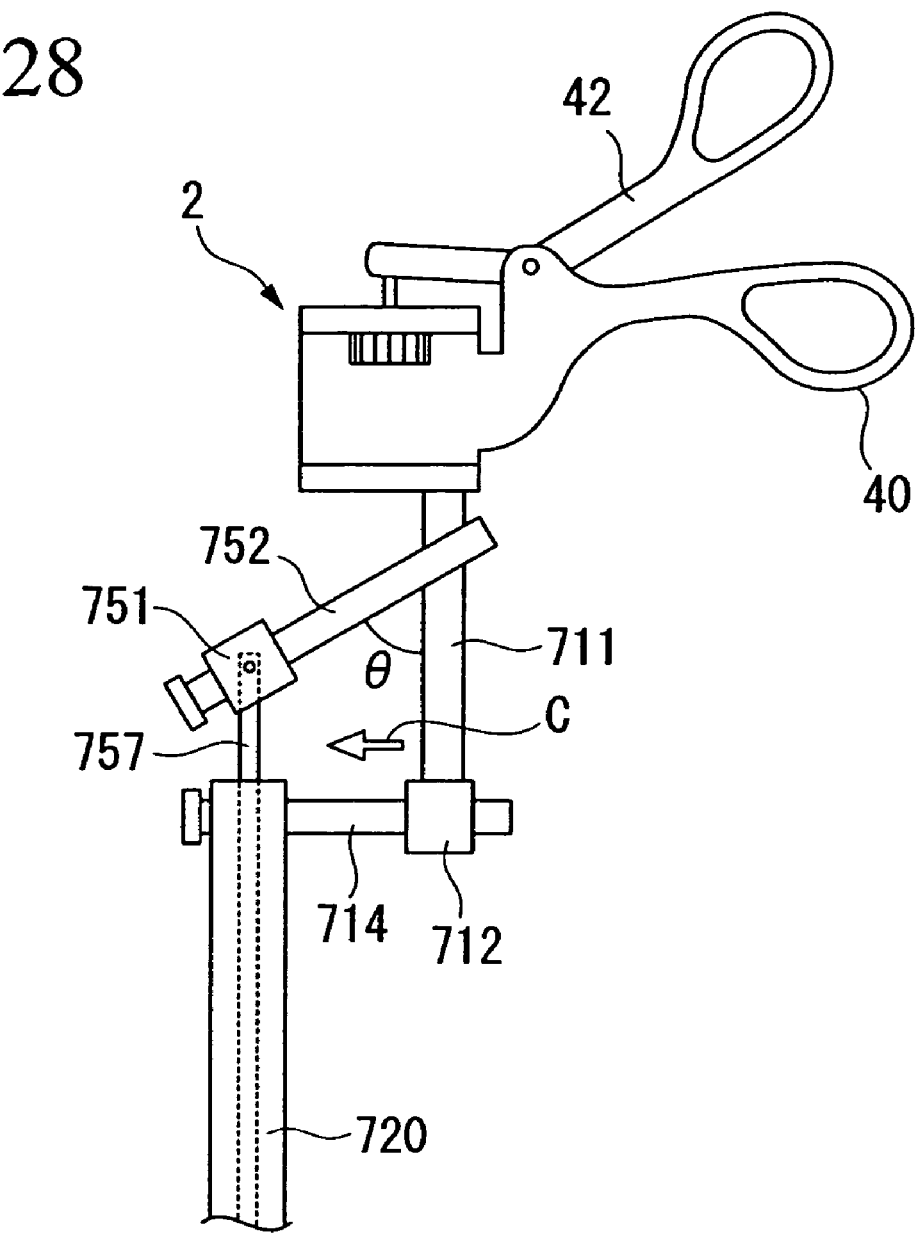
FIG. 28 is a diagram showing a variation of the sliding mechanism on the side close to the operation section in the fifth embodiment.
Figure 29:
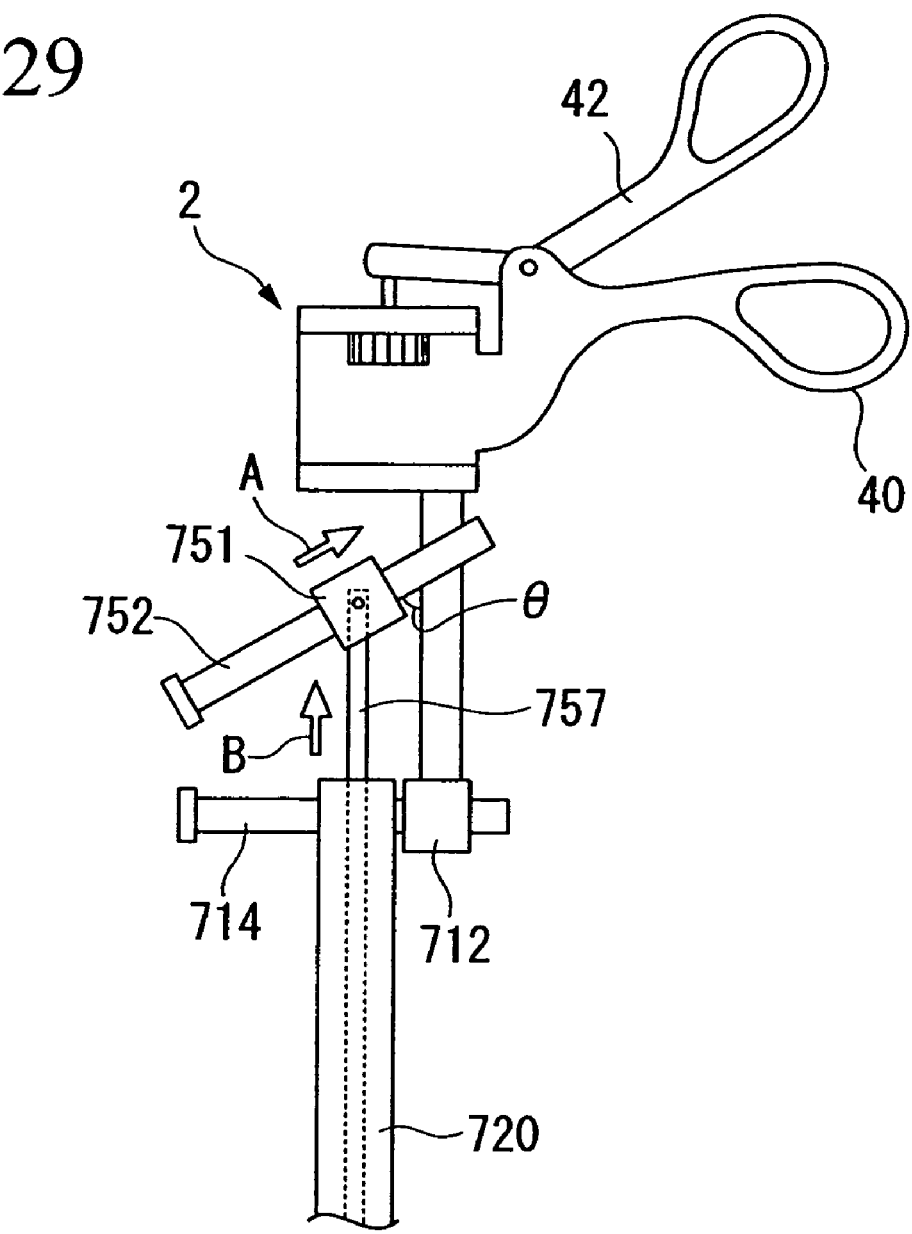
FIG. 29 is a diagram showing another state of the variation shown in FIG. 28.

FIGS. 28 and 29 show a variation of the sliding mechanism on the side close to the operation section 2.

In this variation, a base end of the insertion portion 720 is connected to the guide rail 714, and a base end of a rod member 757 passing through the insertion portion 720 is fastened to a slider 751. To the head of the rod member 757, an end of the link member 730 is rotatably coupled (not shown), similarly to in the embodiment shown in FIGS. 25 and 26. The slider 751 can slide on a guide rail 752 which is fastened to the operation-section support member 711 at a specific angle θ.

The rod member 757 cooperates with sliding operation of the slider 751. For example, in FIG. 29, when the slider 751 slides in a direction indicated by arrow A, the rod member 757 is pulled out from the insertion portion 720, as indicated by arrow B.

Accordingly, also in the present variation, the insertion portion 720 can be easily offset from the axial line between the operation section 2 and the treatment section 4 (see arrow C in FIG. 28), and the force for performing the offset operation can be made constant.

When the above specific angle θ is larger than 60°, the offset operation can be performed with relatively light force.

This variation is not limited to the above-described structure. For example, the guide rail 752 may be fastened to the rod member 757, and a relevant slider may be provided at the operation-section support member 711. Similarly, the guide rail 714 may be fastened to the insertion portion 720, and a relevant slider may be provided at the operation-section support member 711.

Figure 30:
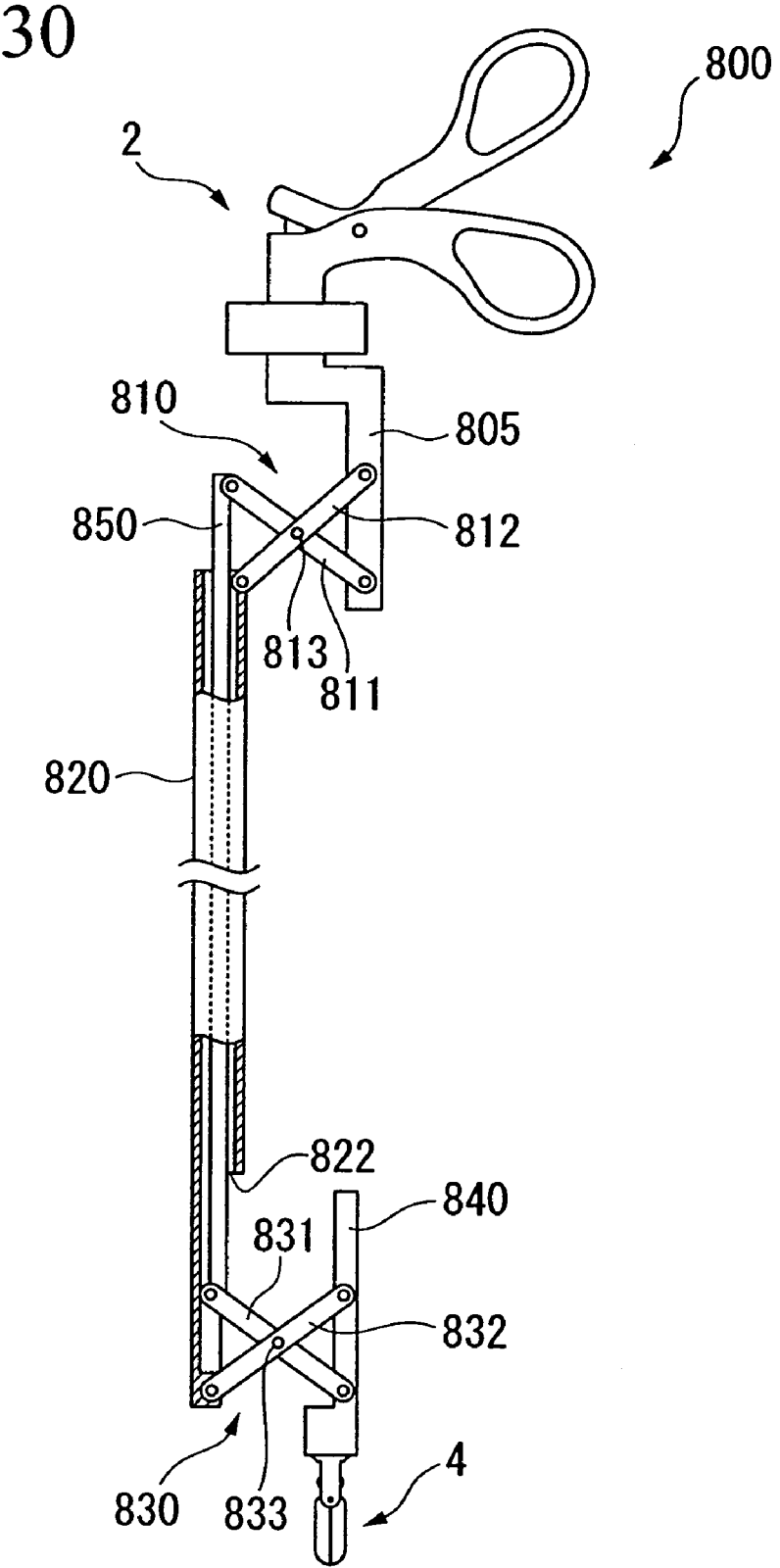
FIG. 30 is a diagram showing another variation of the fifth embodiment.
Figure 31:
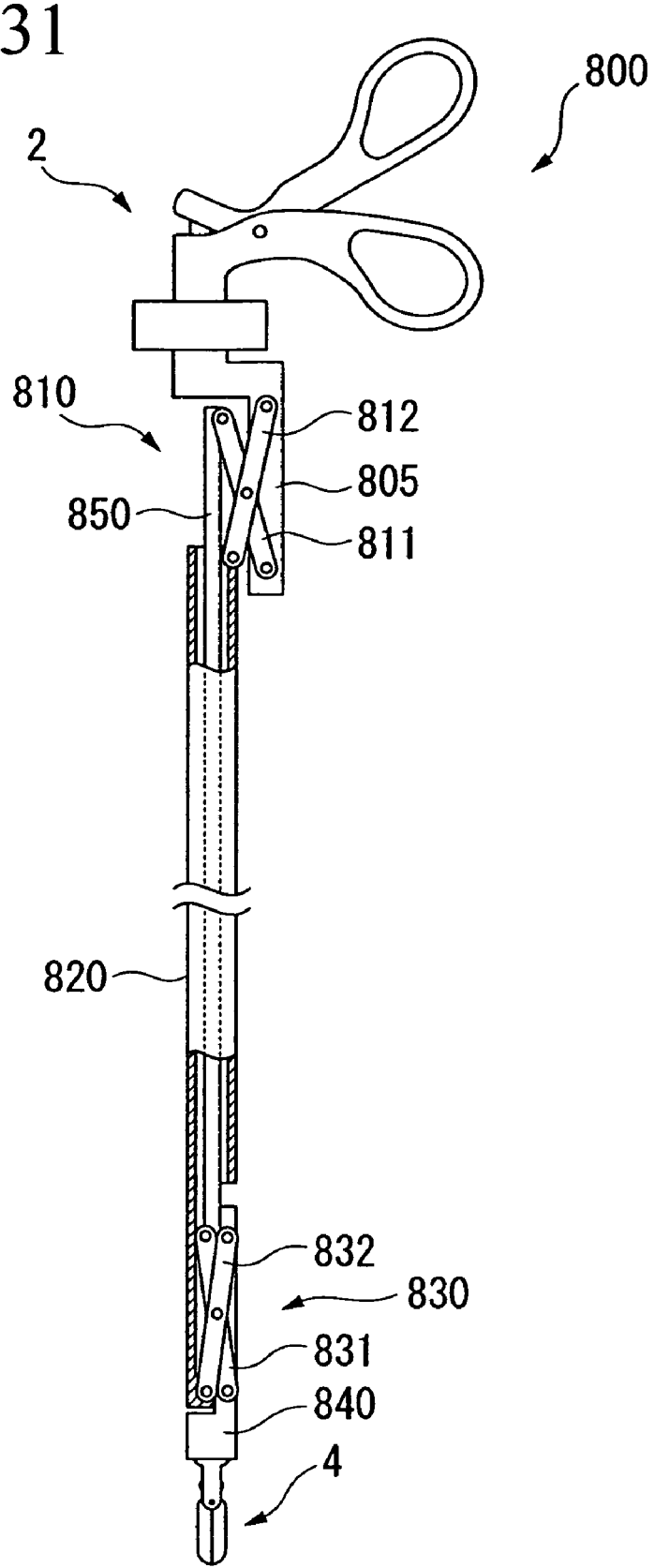
FIG. 31 is a diagram showing another state of the variation shown in FIG. 30.

Next, another variation of the present embodiment is shown in FIGS. 30 and 31, in which X-shaped link structures (810 and 830) are provided for implementing the first and second offset portions.

In FIGS. 30 and 31 (which are schematic diagrams for explaining the link structures), a surgical treatment tool 800 has an operation-section support member 805 connected with the operation section 2. To an end of the operation-section support member 805, an end of a pipe-shaped link member 811 is rotatably coupled, and the other end of the link member 811 is rotatably coupled to an end of a rod member 850 which passes through an insertion portion 820.

A movable bar 812 forms an X shape together with the link member 811 and symmetrically cooperates with the link member 811. An end of the movable bar 812 is rotatably coupled to an end of the insertion portion 820, and the other end of the movable bar 812 can slide from the position shown in FIG. 30 along the axis of the operation-section support member 805 toward the operation section 2, and is also rotatably coupled with the operation-section support member 805. The link member 811 and the movable bar 812 are coupled with each other at the center position of each member, in a relatively rotatable form, by using a pin 813 or the like.

In a head portion (i.e., close to the treatment section 4) of the insertion portion 820, a part of the face which faces the axis of the operation-section support member 805 is removed, thereby producing a recess portion 822. The head portion of the insertion portion 820 is coupled via a pipe-shaped link member 831 with a fittable member 840 which is fittable to the recess portion 822. An end of the link member 831 is rotatably coupled to the other end of the rod member 850, and the other end of the link member 831 is rotatably coupled to the fittable member 840. A movable bar 832 is provided in a manner such that the bar 832 and the link member 831 intersect each other. At the head of the fittable member 840, the treatment section 4 is provided.

An end of the movable bar 832 is rotatably coupled with the head of the insertion portion 820, and the other end thereof is slidable from the position shown in FIG. 30 along the axis of the fittable member 840 in a direction away from the treatment section 4. The link member 831 and the movable bar 832 are coupled with each other at the center position of each member, in a relatively rotatable form, by using a pin 833 or the like.

That is, when the movable bar 832 slides, the angle between the movable bar 832 and the axis of the insertion portion 820 changes. The link member 831 symmetrically cooperates with the operation of the movable bar 832, so that the angle between the link member 831 and the axis of the insertion portion 820 also changes.

In addition, it is possible to form a structure in which a wire, a tube, or the like passes from the operation section 2 to the treatment section 4 via the operation-section support member 805, the link member 811, the rod member 850, and the link member 831. Accordingly, it is possible to easily implement a structure in which the treatment section 4 cooperates with the operation of the operation section 2.

As shown in FIG. 31, when the surgical treatment tool 800 is inserted into a trocar, the surgical treatment tool 800 can have a substantially linear form (that is, the amount of offset measured when the axes of the fittable member 840 and the insertion portion 820 are substantially linearly arranged is zero). In this state, the angle formed between the axis (i.e., along the length) of each of the link members and the movable bars and the axis of the insertion portion 820 is 30° or less. This may provide easier insertion into a trocar.

That is, in the present variation, the first X-shaped link structure 810 functions as a first offset portion, and the second X-shaped link structure 830 functions as a second offset portion (the amount of offset may be approximately 25 mm).

The states shown in FIGS. 30 and 32 can be easily switched between by cooperative expansion and contraction of the first and the second X-shaped link structures 810 and 830 along offset paths for offset and return movements. Specifically, in switching from the state of FIG. 30 to the state of FIG. 31, as the insertion portion 820 moves towards the right in FIG. 30, each X-shaped link structure contracts along the offset path, and the movable heads of the movable bars 831 and 832 respectively slide upward along the axes of the operation-section support member 805 and the fittable member 840, thereby finally creating a folded structure as shown in FIG. 31.

As described above, the X-shaped link structures are provided on the two sides close to the operation section 2 and the treatment section 4. Therefore, the surgical treatment tool 800 can be easily inserted into a trocar, and a head portion (i.e., the treatment section 4) of the surgical treatment tool 800 can be arranged or positioned in a wider area in comparison with conventional tools, similarly to in the above-described embodiments.

In addition, in each X-shaped link structure, the link member and the movable bar form an X shape, thereby producing a truss shape, which improves the rigidity of this portion.

Furthermore, similarly to in the above-described other embodiments, the rod member 850 and the link member 831 respectively have inner holes (not shown) through which a treatment section rotating member and a wire can pass, so as to transmit the operation of the operation section 2 to the treatment section 4.

Similarly to in the above-described other embodiments, each X-shaped link structure is not limited to the structure shown in FIGS. 30 and 31, and the arrangement of the movable bar and the link member can be changed to have an inverted form. That is, one end of a link member corresponding to the movable bar 832 may be rotatably connected to the head of the rod member 850, and the other end thereof may be rotatably connected to the fittable member 840, while one end of a movable bar corresponding to the link member 831 may be rotatably coupled to a head portion of the insertion portion 820, and the other end thereof may be slidably and rotatably connected to the fittable member 840. Similarly, an end of a link member corresponding to the movable bar 812 may be rotatably connected to the base end of the rod member 850, while a movable bar corresponding to the link member 811 may be rotatably coupled to a base end portion of the insertion portion 820. In accordance with such a structure, the shape of the insertion portion 820 and a positional relationship along the axis between the insertion portion 820 and the rod member 850 are slightly different from the states shown in FIGS. 30 and 31.

Regarding the structure and the operation of each of the operation section 2 and the treatment section 4 in the present embodiment, the various forms or modes in the above-described other embodiments can be used.

What is claimed is:

1. A medical instrument for an endoscope, wherein the instrument is configured to pass through an opening in a body wall of a living body, the medical instrument comprising:
   a first insertion portion having a base end portion to which an operation section is connected;
   a first offset portion extending outward from an axis of the first insertion portion;
   a second insertion portion having a base end portion joined to the first offset portion and an element extending parallel to the axis of the first insertion portion;
   a second offset portion which is joined to a head portion of the second insertion portion and reaches an extension of the axis of the first insertion portion;
   a third insertion portion which is joined to the second offset portion and has a portion arranged on an axis which is substantially the same as at least a part of the axis of the first insertion portion;
   an inner hole formed through the first insertion portion, the first offset portion, the second insertion portion, the second offset portion, and the third insertion portion; and
   a response mechanism configured to offset the third insertion portion from an axis of the second insertion portion, in response to an offset operation of the first insertion portion from the axis of the second insertion portion, in a manner that maintains a constant distance in an axial direction measured from the base end portion of the first insertion portion to a head portion of the third insertion portion.

2. The medical instrument for an endoscope according to claim 1, wherein the second insertion portion and the second offset portion are coupled to each other in a freely rotatable form, and the second offset portion and the third insertion portion are coupled to each other in a freely rotatable form.

3. The medical instrument for an endoscope according to claim 2, wherein the first insertion portion and the first offset portion are coupled to each other in a freely rotatable form, the first offset portion and the second insertion portion are coupled to each other in a freely rotatable form, and the second offset portion is arranged parallel to the first offset portion.

4. The medical instrument for an endoscope according to claim 2, wherein the first offset portion and the second offset portion move together in a manner such that a variation in a distance from a joint between the second insertion portion and the second offset portion to an extension of the axis of the first insertion portion coincides with a variation in a distance from a joint between the second insertion portion and the first offset portion to the axis or the extension thereof of the first insertion portion.

5. The medical instrument for an endoscope according to claim 1, wherein the second offset portion is freely capable of expansion and contraction in a direction substantially perpendicular to the axis of the first insertion portion.

6. The medical instrument for an endoscope according to claim 5, wherein the first offset portion and the second offset portion move together in a manner such that a variation in a distance from a joint between the second insertion portion and the second offset portion to an extension of the axis of the first insertion portion coincides with a variation in a distance from a joint between the second insertion portion and the first offset portion to the axis or the extension thereof of the first insertion portion.

7. The medical instrument for an endoscope according to claim 1, wherein the second insertion portion is set to have a length greater than that of a trocar through which the second insertion portion is inserted.

8. The medical instrument for an endoscope according to claim 1, wherein a clipping member which can be freely opened and closed is provided at a head portion of the third insertion portion, the operation section is provided at the base end portion of the first insertion portion, and a driving force transmitting member is inserted through the inner hole so as to connect the operation section and the clipping member.

9. The medical instrument for an endoscope according to claim 1, wherein an imaging device is provided at a head of the third insertion portion, and a video cable for the imaging device is pulled out from the base end portion of the first insertion portion.

10. The medical instrument for an endoscope according to claim 1, wherein a treatment tool for performing treatment on the living body is inserted into the inner hole.

11. The medical instrument for an endoscope according to claim 1, wherein the offset operation of the third insertion portion from the axis of the second insertion portion is performed simultaneously with the offset operation of the first insertion portion.

12. The medical instrument for an endoscope according to claim 1, wherein:
   the response mechanism has a link member that links the first insertion portion with the third insertion portion; and
   the link member operates in response to the offset operation of the first insertion portion, and the third insertion portion moves offset from the axis of the second insertion portion in response to the operation of the link member.

* * * * *